United States Patent
Wong et al.

(10) Patent No.: US 8,389,544 B2
(45) Date of Patent: Mar. 5, 2013

(54) ISOQUINOLONE COMPOUNDS AS SUBTYPE-SELECTIVE AGONISTS FOR MELATONIN RECEPTORS $MT_1$ AND $MT_2$

(75) Inventors: Yung Hou Wong, Hong Kong (CN); Maurice Kwok Chung Ho, Hong Kong (CN); Yueqing Hu, Hong Kong (CN); David Charles New, Hong Kong (CN); Xixin He, Honolulu, HI (US); Haihong Pang, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 514 days.

(21) Appl. No.: 12/523,532

(22) PCT Filed: Jan. 17, 2007

(86) PCT No.: PCT/CN2007/000164
§ 371 (c)(1), (2), (4) Date: Jul. 30, 2010

(87) PCT Pub. No.: WO2008/092292
PCT Pub. Date: Aug. 7, 2008

(65) Prior Publication Data
US 2010/0317691 A1    Dec. 16, 2010

(51) Int. Cl.
*A61K 31/47* (2006.01)
*C07D 217/23* (2006.01)
(52) U.S. Cl. ........ 514/309; 546/141
(58) Field of Classification Search ............ 514/309; 546/141
See application file for complete search history.

(56) References Cited

U.S. PATENT DOCUMENTS 6,908,931 B2 * 6/2005 Dubowchik et al. .......... 514/307
7,214,689 B2 * 5/2007 Poissonnier-Durieux et al. .......................... 514/307

* cited by examiner

*Primary Examiner* — Raymond Henley, III
(74) *Attorney, Agent, or Firm* — Saliwanchik, Lloyd & Eisenschenk

(57) ABSTRACT

A method of treating, preventing, or ameliorating a pathological condition associated with a melatonin receptor in a mammal by using a pharmaceutical composition containing a compound of formula (I) as a ligand interacting with the melatonin receptor,

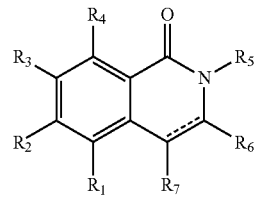

$R_1$, $R_2$, $R_3$, $R_4$ and $R_7$ are independently H, halo, alkyloxyl, alkyl or hydroxyl, provided that one of $R_1$, $R_2$, $R_3$ and $R_7$ is X—$(CH_2)_n$—$R_8$; $R_5$ is alkyl or arylalkyl; $R_6$ is H or alkyl; X is a bond, O, S, SO, $SO_2$, CO or NH; n=0-10; $R_8$ is alkenyl, substituted or unsubstituted aryl, $NR_9R_{10}$, or $OR_9$; $R_9$ is H, substituted or unsubstituted arylmethyl, or alkenyl; and $R_{10}$ is H or alkyl.

20 Claims, 8 Drawing Sheets

ISOQUINOLONE COMPOUNDS AS SUBTYPE-SELECTIVE AGONISTS FOR MELATONIN RECEPTORS MT$_1$ AND MT$_2$

FIELD OF THE INVENTION

The invention relates to isoquinolone derivatives and their use as therapeutic agents. In particular, the invention relates to isoquinolone compounds that are capable of modulating melatonin receptors and to pharmaceutical compositions containing such compounds for treating disorders or pathological conditions associated with melatonin receptors in mammalian subjects.

BACKGROUND OF THE INVENTION

Melatonin (N-acetyl-5-methoxytryptamine) is a hormone primarily synthesized and secreted by the pineal gland and has been shown to regulate mammalian circadian rhythms and reproductive functions (Kennaway and Wright, 2002; Guerrero and Reiter, 2002). Melatonin is a lipophilic hormone widely distributed throughout the nervous system, blood and peripheral tissues of mammals (Vaughan et al., 1978; Rogawski et al., 1979). It exerts its biological effects through interaction with specific melatonin receptors. Two human melatonin receptors, MT$_1$ and MT$_2$, have been identified and cloned, both possessing a similar binding affinity for melatonin (Reppert et al., 1994, 1995). These receptors are G protein-coupled receptors, indicating a triggering mechanism via G protein mediated signaling pathways. The G proteins, in turn, directly or indirectly (via a second messenger) regulate various effector systems. Due to different classes of G proteins that are able to mediate the downstream signaling pathways of melatonin receptors (New et al, 2003), MT$_1$ and MT$_2$ can trigger many distinct signal transduction cascades, leading to the activation of various unique cellular responses (Witt-Enderby et al., 2003).

The melatonin receptors MT$_1$ and MT$_2$ are expressed in a wide variety of tissues within the body. The MT$_1$ receptor is expressed in the suprachiasmatic nucleus (SCN) of the hypothalamus within the brain, the cardiac vessels and various regions of the brain and peripheral tissues. MT$_1$ receptors are also found in normal and malignant breast tissue (Dillon et al, 2002). MT$_2$ receptors are more localized and found in the cerebellum and SCN within the brain, retina, ovary, kidneys and cardiac vessels. Both receptors are thought to play a role in mediating the sleep/wake cycle by modulating the body's circadian rhythms (Dubocovich et al., 1998) but while the MT$_1$ receptor is thought to regulate sleepiness, the MT$_2$ receptor is thought to help regulate sleep-wake cycles, and while MT$_1$ receptors constrict cardiac vessels, MT$_2$ receptors dilate them (Doolen et al, 1998). Furthermore, MT$_2$ receptors are involved in inflammatory responses. Therefore, with the wide distribution of both receptors in many different tissues within the body, it is not surprising that melatonin is involved in numerous physiological processes of the body.

Melatonin has been implicated in the regulation of a number of physiological processes (Pandi-Perumal et al, 2006) and thus, has been used in the treatment of many biological disorders. It is widely used in the treatment of chronobiological disorders such as seasonal affective disorders (SAD) (Rosenthal et al., 1986), primary and secondary insomnia, and sleep disorders caused by blindness (Nakagawa et al., 1992), shift work (Sack et al., 1992) and jet lag (Arendt et al., 1991). Melatonin has also been linked to retinal physiology (Dubocovich et al., 1997), blood pressure regulation (Doolen et al., 1998), and in the regulation of the immune system (Guerrero and Reiter, 2002), and inflammation (Cuzzocrea and Reiter, 2002). In addition, melatonin has been shown to have a strong effect against cancer and tumor growth (Reiter, 2003; Blask et al, 2002). Furthermore, in numerous recent investigations, melatonin has been reported to inhibit the growth and progression of a variety of tumor cells including breast cancer, ovarian carcinoma, endometrial carcinoma, melanoma, prostate tumor and intestinal tumor cells (Pandi-Perumal et al. 2006).

Recent evidence also indicate that melatonin may be beneficial in the treatment of psychiatric disorders (bipolar, depression and anxiety disorders, schizophrenia, epilepsy and epileptic seizures), neurodegenerative diseases (Parkinson's disease (PD), Alzheimer's disease (AD), Huntington's disease, amyotrophic lateral sclerosis, muscular sclerosis), stroke and neuroendocrine disorders (peptic ulceration, psoriasis). A recent study offers experimental evidence supporting melatonin as a promising therapeutic agent in the treatment of PD (Khaldy et al., 2003). Melatonin has also been shown to confer a protective effect against epilepsy in humans (Molina-Carballo et al., 1997) and rats (Bikjdaouene et al., 2003) and this effect is thought to occur by increasing GABAergic neurotransmission (Acuna-Castroviejo et al., 1995). Melatonin also has shown to confer beneficial effects in Alzheimer's patients. A recent report has indicated that patients with AD exhibit reduced expression of the melatonin receptor subtype MT$_2$ (Savaskan et al., 2005). Administration of melatonin to AD patients have garnered promising results, including improved cognitive function, improved sleep and a significant reduction in the rate of disease progression (Maurizi, 2001; Cardinali, 2003).

Melatonin also plays a role in neuroprotection. Recent reports demonstrate the involvement of melatonin in neuroprotection after an acute cerebral ischemic stroke. Studies on animal models of focal cerebral ischemia indicate that melatonin confers a marked neuroprotective effect (Kilic et al., 2005; Lee et al., 2005; Macleod et al., 2005) and exerts anti-inflammatory effects (Pei and Cheung, 2004), and results have suggested that melatonin may be a good candidate as a neuroprotective drug for stroke in humans (Macleod et al., 2005). Melatonin's neuroprotective action is thought to occur via its antioxidant and free radical scavenging activity (Lee et al., 2005).

Despite the modulatory effects of melatonin on various effector systems, its use in clinical applications has been limited by its short biological half-life, poor oral bioavailability and ubiquitous action (Uchikawa et al., 2002). Therefore, in recent years, much work has been undertaken to identify or develop melatonergic agonists that are more metabolically stable than melatonin, exhibit higher affinity to the MT$_1$ and MT$_2$ receptors, and most importantly, show selectivity towards one receptor sub-type over the other. Melatonergic agonists of synthetic origin mimic the signal cascade generated by melatonin by binding to the melatonin receptors, MT$_1$ and MT$_2$. They are of immense value for the physiological study of the different melatonin receptor subtypes and help delineate the manner by which melatonin modulates and triggers other effector systems.

As melatonin has been shown to mediate sleep-wake cycles by broadly targeting receptors, melatonergic agonists that demonstrate melatonergic properties and high affinity and selectivity for one or both of the melatonergic receptor sub-types are valuable both as therapeutic agents and research tools. They are promising therapeutic agents for the treatment of insomnia and circadian-related disorders, as well as in the treatment of other disorders related to melatonin as mentioned above.

In addition to the hormone melatonin, there are several other known melatonergic ligands that interact with the melatonin receptors. These include 2-iodomelatonin and N-acetylserotonin, which, like melatonin, bind to both $MT_1$ and $MT_2$ receptors albeit with different affinities. These agonists have been used for pharmacological evaluation of the receptor subtypes but their use has been limited by their lack of selectivity between the two receptor subtypes. Further, they are not promising drug candidates. Ligands to the melatonin receptors which exhibit selectivity towards one of the receptors are of greater pharmacological and therapeutic value. Therefore, in recent years, many different research groups have used medicinal chemistry to synthesize agonists that exhibit greater selectivity and higher binding affinities.

Most of the known melatonin receptor ligands are developed based on the indole structure of melatonin. Critical features include the 5-methoxyl group (Chong et al., 1993; Mor et al., 1998; Sicsic et al., 1997; Sugden et al., 1995) and the 3-ethyl amide chain (Grol and Jansen, 1996). The relative distance and conformations of the methoxyl and the amide group on melatonin are some of the critical factors determining the potency and efficacy of the ligands. The alkyl chain attached to the amide carbonyl group has a limitation of <3 carbons in length in order to retain a high affinity (Sugden et al., 1995). Tolerance and specificity of C2 and C6 substitutions have been studied intensively (Spadoni et al., 1993; Sugden et al., 1995). Other melatonin ligand structures adopt various heterocyclic scaffolds such as tricyclic and tetracyclic indole-based rings, indane, naphthalene, tetraline, quinoline, benzoxazole, benzofuran, etc. (Zlotos, 2005).

In plants, alkaloids are involved in defense mechanisms against herbivores and pathogens. Published reports have indicated that alkaloids in plants confer neuroprotective activities. They have also been reported to possess antiviral, antimicrobial and immunomodulating activities (Hudson, 1990; Huang, 1999), as well as potent anti-tumor agents (Cragg et al., 1997; Cragg and Phil, 1999).

Although U.S. application Ser. Nos. 10/135,247 and 10/738,964 as well as PCT Application Publications WO/2005/075431 A1 and WO/2005/075432 A1 have disclosed some isoquinolone derivatives, prior to the present invention, the applicants are not aware of any isoquinolone derivatives that possess melatonin receptor agonist activity.

References

Acuna-Castroviejo et al. (1995) Cell protective role of melatonin in the brain. *Journal of Pineal Research* 16:100-112.

Arendt, J. (1991) Melatonin in humans: jet lag and after. *Adv Pineal Res* 5:299-302.

Bikjdaouene et al. (2003) Changes in brain amino acids and nitric oxide after melatonin administration in rats with pentylenetetrazole-induced seizures. *Journal of Pineal Research* 25:54-60.

Blask, D. E., Sauer, L. A., and Dauchy, R. T. (2002) Melatonin as a chronobiotic/anticancer agent: cellular, biochemical and molecular action and therapeutic implications for circadian-based cancer therapy. *Current Topics in Medicinal Chemistry* 2:113-132.

Cardinali, D. P. (2003) Clinical perspectives for the use of melatonin as a neuroprotective chronobiotic in Alzheimer's disease. *Akualnosci Neurologiczne* 2:188-204.

Cragg, G. M., Newman, D. J., Weiss, R. B. (1997) Coral Reefs, forests, and thermal vents: the worldwide exploration of nature for novel anticancer agents. *Seminars in Oncology* 24:156-163.

Cragg, G. M. and Phil, D. J. (1999) Discovery and development of anti-neoplastic agents from natural sources. *Cancer Invest* 17: 153-163.

Cuzzocrea, S, and Reiter, R. J. (2002) Pharmacological actions of melatonin in acute and chronic inflammation. *Curr Top Med Chem* 2:153-165.

Dillon, D. C., Easley, S. E., Asch, B. B., Cheney, R. T., Brydon, L., Jockers, R., Winston, J. 1., Hurd, T., and Asch, H. L. (2002) Differential expression of high-affinity melatonin receptor (MT1) in normal and malignant human breast tissue. *American Journal of Clinical Pathology* 118: 451-458.

Doolen, S., Krause, D. N., Dubocovich, M. L., and Duckles, S. P. (1998) Melatonin mediates two distinct responses in vascular smooth muscle. *European Journal of Pharmacology* 345:67-69.

Dubocovich, M. L., Masana, M. I., Iacob, S., and Sauri, D. M. (1997) Melatonin receptor agonists that differentiate between the human Mel1a and Mel1b recombinant subtypes are used to access the pharmacological profile of the rabbit retina ML1 presynaptic heteroreceptor. *Naunyn-Schmiedeberg's Archives of Pharmacology* 335:365-375.

Dubocovich, M. L., Yun, K., μl-Ghoul, W. M., Benloucif, S., and Masana, M. I. (1998) Selective MT2 melatonin receptor antagonists block melatonin-mediated phase advances of circadian rhythms. *FASEB* 12:1211-1220.

Guerrero, J. M. and Reiter, R. J. (2002) Melatonin-immune system relationships. *Current Topics in Medicinal Chemistry* 2:167-169.

Hudson, J. B. (1990) Alkaloids. In: Antiviral compounds from plants. pp. 83-87. CRC Press, Basa Raton.

Huang, K. C. (1999) The Pharmacology of Chinese Herbs. 2nd edition, CRC Press LLC.

Kennaway, D. J. and Wright, H. (2002) Melatonin and circadian rhythms. *Curr Top Med Chem* 2:199-209.

Khaldy, H., Escames, G., Leon, J., Bikjdaouene, L., and Acuna-Castroviejo, D. (2003) Synergistic effects of melatonin and deprenyl against MPTP-induced mitochondrial damage and DA depletion. *Neurobiology of Aging* 24:491-500.

Kilic, U., Kilic, E., Reiter, R. J., Bassetti, C. L. and Hermann, D. M. (2005) Signal transduction pathways involved in melatonin-induced neuroprotection after focal cerebral ischemia in mice. *J Pineal Res* 38:67.

Lee, E.-J., Lee, M-Y., Chen, H-Y., Hsu, Y-S., Wu, T-S., Chen, S-T. and Chang, G-L. (2005) Melatonin attenuates gray and white matter damage in a mouse model of transient focal cerebral ischemia. *J Pineal Res* 38: 42.

Macleod, M. R., O'Collins, T., Horky, L. L., Howells, D. W., and Donnan, G. A. (2005) Systemic review and meta-analysis of the efficacy of melatonin in experimental stroke. *J Pineal Res* 38: 35.

Maurizi, C. P. (2001) Alzheimer's disease: roles for mitochondrial damage, the hydroxyl radical and cerebrospinal fluid deficiency of melatonin. *Medical Hypotheses* 57:455-462.

Molina-Carballo et al. (1997) Utility of high doses of melatonin as adjunctive therapy in a child with severe myoclonic epilepsy: two years' experience. *Journal of Pineal Research* 27:202-209.

Nakagawa, H., Sack, R. L., and Lewy, A. J. (1992) Sleep propensity free-runs with the temperature, melatonin and cortisol rhythms in a totally blind person. *Sleep* 15:330-336.

New D. C., Tsim S. T. and Wong Y. H. (2003) G protein-linked effector and second messenger systems involved in melatonin signal transduction. *Neurosignals* 12:59-70.

Pandi-Perumal, S. R., Srinivasan, V., Maestroni, G. J. M., Cardinali, D. P., Poeggeler, B., and Hardeland, R. (2006) Nature's most versatile biological signal? *FEBS Journal* 273:2813-2838.

Pei, Z. and Cheung, R. T. (2004) Pretreatment with melatonin exerts anti-inflammatory effects against ischemia/reperfusion injury in a rat middle cerebral artery occlusion stroke model. *J Pineal Res* 37:85-91.

Reiter, R. J. (2003) Melatonin: Clinical relevance. *Best Practice and Research Clinical Endocrinology and Metabolism* 17:273-285.

Reppert, S. M., Weaver, D. R., and Ebisawa, T. (1994) Cloning and characterization of a mammalian melatonin receptor that mediates reproductive and circadian responses. *Neuron* 113:1177-1185.

Reppert et al. (1995) Molecular characterization of a second melatonin receptor expressed in human retina and brain: the Mel1b melatonin receptor. *Proc Natl Acad Sci USA* 92:8734-8738.

Rogawski, M. A., Roth, R. H., and Aghajanian, G. K. (1979) Melatonin: Deacetylation to 5-methoxytryptamine by liver but not brain aryl acylamidase. *J Neurochem* 32:1219-1226.

Rosenthal et al. (1986) Melatonin in seasonal affective disorder and phototherapy. *J Neural Transm Suppl* 21:257-267.

Sack, R. L., Blood, M. L., and Lewy, A. J (1992) Melatonin rhythms in night shift workers. *Sleep* 15:434-441.

Savaskan, E., Ayoub, M. A., Ravid, R., Angeloni, D., Fraschini, F., Meier, F., Eckert, A., Muller-Spahn, F., and Jockers, R., (2005) Reduced hippocampal MT2 melatonin receptor expression in Alzheimer's disease. *J Pineal Res* 38:10.

Uchikawa et al. (2002) Synthesis of a novel series of tricyclic indan derivatives as melatonin receptor agonists. *J Med Chem* 45:4222-39.

Vaughan et al. (1978) Melatonin concentration in human blood and cerebrospinal fluid: Relationship to stress. *J Clin Endocrinol Metab* 47:220-223.

Witt-Enderby et al. (2003) Melatonin receptors and their regulation: biochemical and structural mechanisms. *Life Sciences* 72:2183-2198.

SUMMARY OF THE INVENTION

In one aspect of the present invention, there is provided a method of treating, preventing, or ameliorating a pathological condition in a mammal, wherein said pathological condition is associated with a melatonin receptor, comprising a step of administering to said mammal a therapeutically effective amount of an isoquinolone derivative of formula (I):

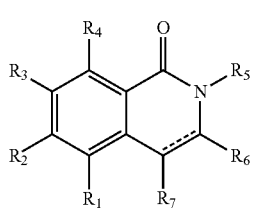

(I)

where R1-R7 are each independently hydrogen or a substituent. A substituent is an atom or group of atoms substituted in place of the hydrogen atom. The substitution can be achieved by means known in the field of chemical synthesis. For example, through a proper design, high through-put combinatorial synthesis is capable of producing a large library of derivatives with various substituents attached to various positions of the backbone of the parent compound. The isoquinolone derivative of the present invention may then be selected by its desired melatonergic properties. For a large library, the selection may be accomplished by a high throughput screen method. As a therapeutic agent, the compound of formula (I) may be in a form of functional derivatives as defined below.

As another aspect of the present invention, there is provided a series of isoquinolone derivatives that possess melatonergic properties with high affinity for melatonergic receptors, with or without high selectivity towards one sub-type of the receptor over the other. These isoquinolone derivatives are of the following formula (II)

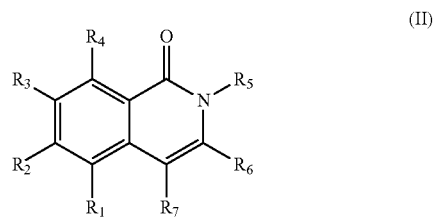

(II)

Wherein $R_1$, $R_2$, $R_3$, $R_4$ and $R_7$ are independently H, halo, alkoxy, alkyl or hydroxyl, provided that one of $R_1$, $R_2$, $R_3$ and $R_7$ is $X-(CH_2)_n-R_8$;

$R_5$ is alkyl or arylalkyl;

$R_6$ is H or alkyl;

X is a bond, O, S, SO, $SO_2$, CO or NH;

n=0-10;

$R_8$ is alkenyl, substituted or unsubstituted aryl, $NR_9R_{10}$, or $OR_9$;

$R_9$ is H, substituted or unsubstituted arylmethyl, or alkenyl; and $R_{10}$ is H or alkyl.

It is contemplated, as a person with ordinary skill in the art would understand, that the above compounds may be made in various possible racemic, enantiomeric or diastereoisomeric isomer forms, may form salts with mineral and organic acids, and may also form derivatives such as N-oxides, prodrugs, bioisosteres. "Prodrug" means an inactive form of the compound due to the attachment of one or more specialized protective groups used in a transient manner to alter or to eliminate undesirable properties in the parent molecule, which is metabolized or converted into the active compound inside the body (in vivo) once administered. "Bioisostere" means a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Making suitable prodrugs, bioisosteres, N-oxides, pharmaceutically acceptable salts or various isomers from a known compound (such as those disclosed in this specification) are within the ordinary skill of the art. Therefore, the present invention contemplates all suitable isomer forms, salts and derivatives of the above disclosed compounds.

In the context of the present invention, the term "functional derivative" means a prodrug, bioisostere, N-oxide, pharmaceutically acceptable salt or various isomer from the above-disclosed specific compound, which may be advantageous in one or more aspects compared with the parent compound. Making functional derivatives may be laborious, but the technologies involved are well known in the art. Various high-throughput chemical synthetic methods are available. For example, combinatorial chemistry has resulted in the rapid expansion of compound libraries to be coupled with various highly efficient bio-screening technologies.

In another aspect of the present invention, there is provided a method of synthesizing and identifying a melatonin receptor agonist to be used as therapeutic agents for treating a number of diseases associated with melatonin receptors. The method comprises the steps of (a) design and synthesis of isoquinolone derivatives of formula (I) with a variety of substituents at different positions and (b) performing an assay on an isoquinolone derivative to determine any effect related to a melatonin receptor or any melatonin agonist activity. In step (a), the isoquinolone derivative may be obtained on an individual basis through conventional organic synthesis, where a particular derivative is envisioned with substitution at one or more given positions of formula (I). The isoquinolone derivatives may also be obtained through solid phase combinatorial synthesis using isoquinolone building blocks. Libraries of isoquinolone derivatives may be obtained at once through combinatorial synthesis using IRORI technology involving microkan reactors and radio refrequency tags. In step (b), if a melatonin receptor related effect is observed, specificity of the effect towards a particular melatonin receptor sub-type may also be further determined.

For the purpose of understanding the specification and construing the scope of the claims, throughout the specification and claims, the word "a" means "one or more". For instance, "performing an assay on an isoquinolone derivative" is the same as "performing one or more assays on one or more isoquinolone derivatives".

As another aspect of the present invention, it is also contemplated that the compound of formula (II) is further incorporated in a pharmaceutical composition for treating or preventing a pathological condition or symptom in a mammal, wherein the pathological condition or symptom can be alleviated and prevented by modulation of the activity of a melatonin receptor.

As another aspect of the present invention, there is provided a method for treating, preventing, or ameliorating a pathological condition in a mammal, where the pathological condition is alleviated or prevented by the modulation of the activity of a melatonin receptor and where the method comprises administering to the mammal with pathological condition a therapeutically effective amount of a compound of formula (I). The melatonin receptor is $MT_1$, $MT_2$ or both.

As another aspect, there is provided a method of modulating $MT_1$ or $MT_2$ receptor activity by contacting the receptor with a compound of formula (I) either in vitro or in vivo for the purpose of therapy or scientific research.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS

I. Obtaining Isoquinolone Derivatives with Melatonergic Agonist Activity

Isoquinolone derivatives may be obtained by extracting them from natural sources, such as plants, or by chemical synthesis. Indeed, both natural resources and chemical synthesis were utilized in the present invention.

Figure 1:
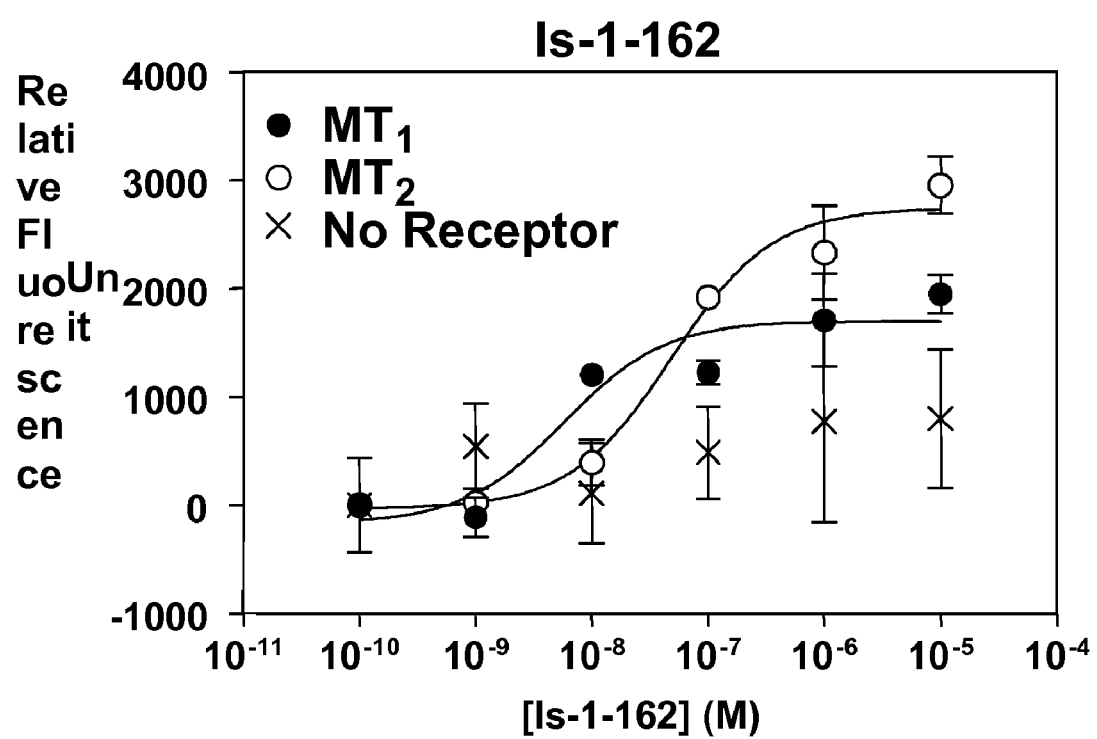
FIG. 1 shows a dose-response curve of Isoquinolone compound IS005.
Figure 2:
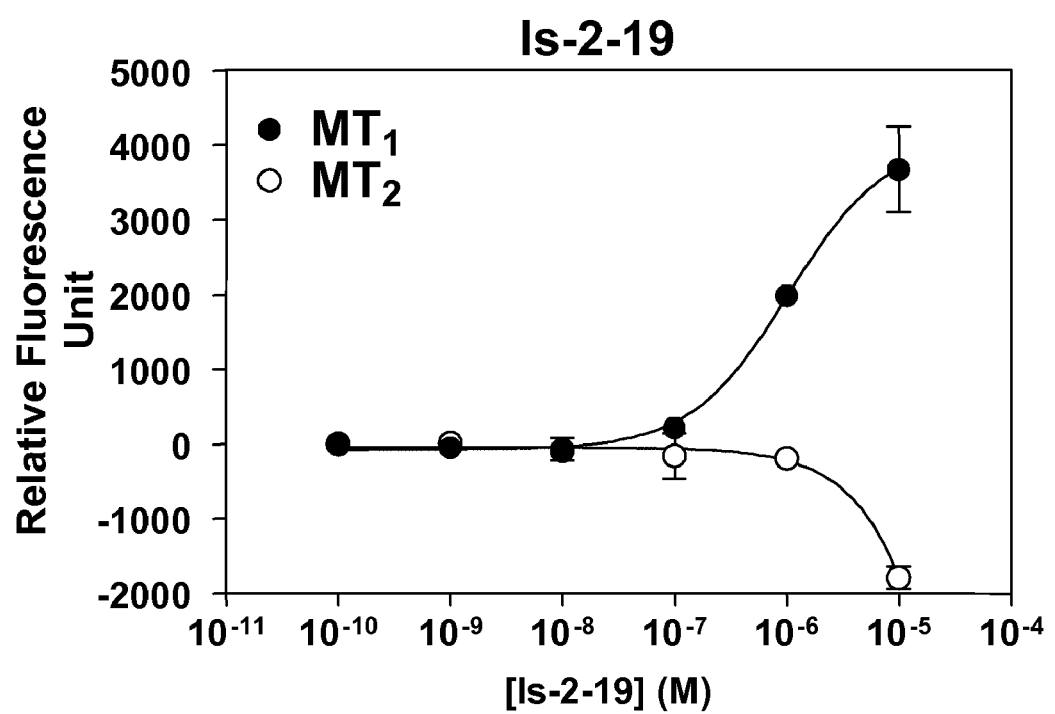
FIG. 2 shows a dose-response curve of Isoquinolone compound IS030.
Figure 3:
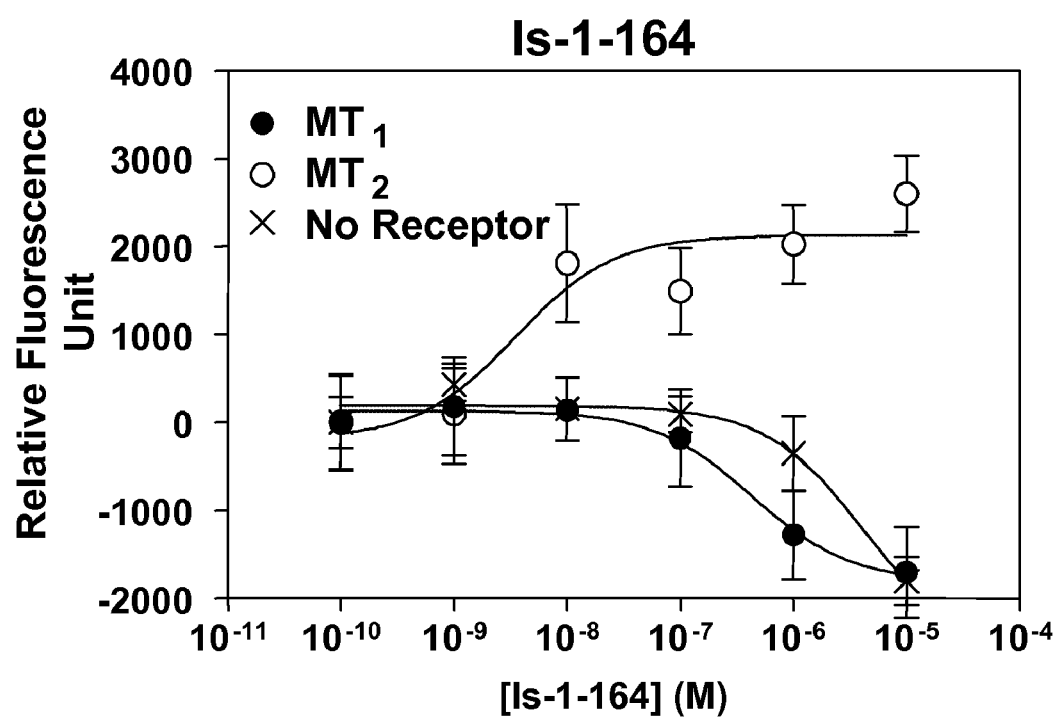
FIG. 3 shows a dose-response curve of Isoquinolone compound IS007.
Figure 4:
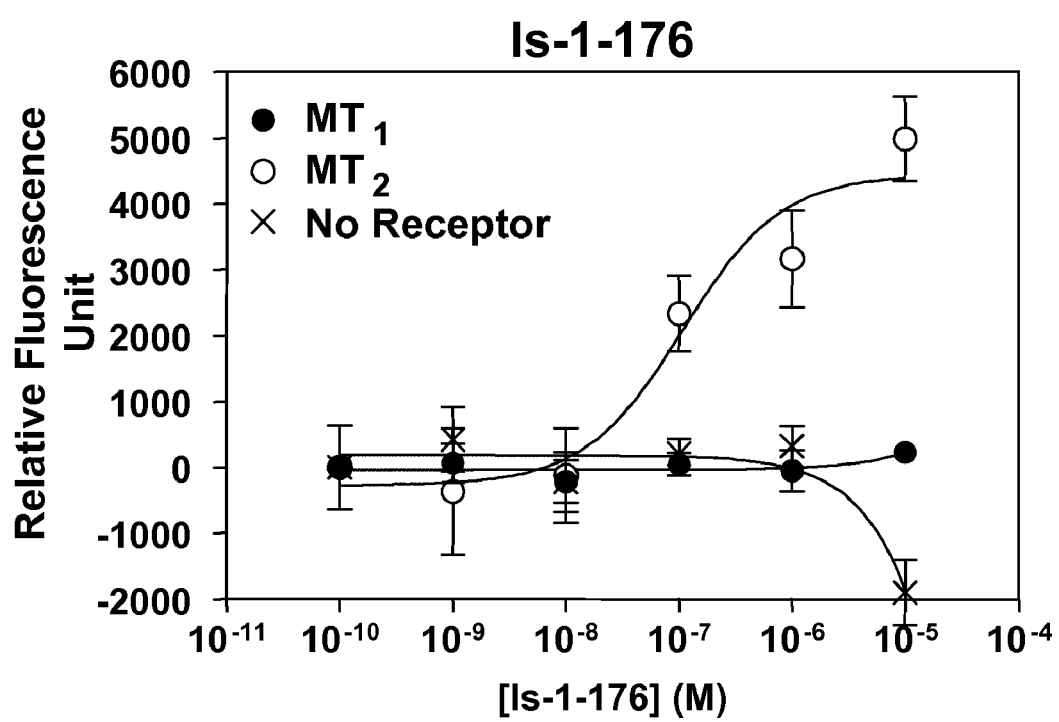
FIG. 4 shows a dose-response curve of Isoquinolone compound IS017.
Figure 5:
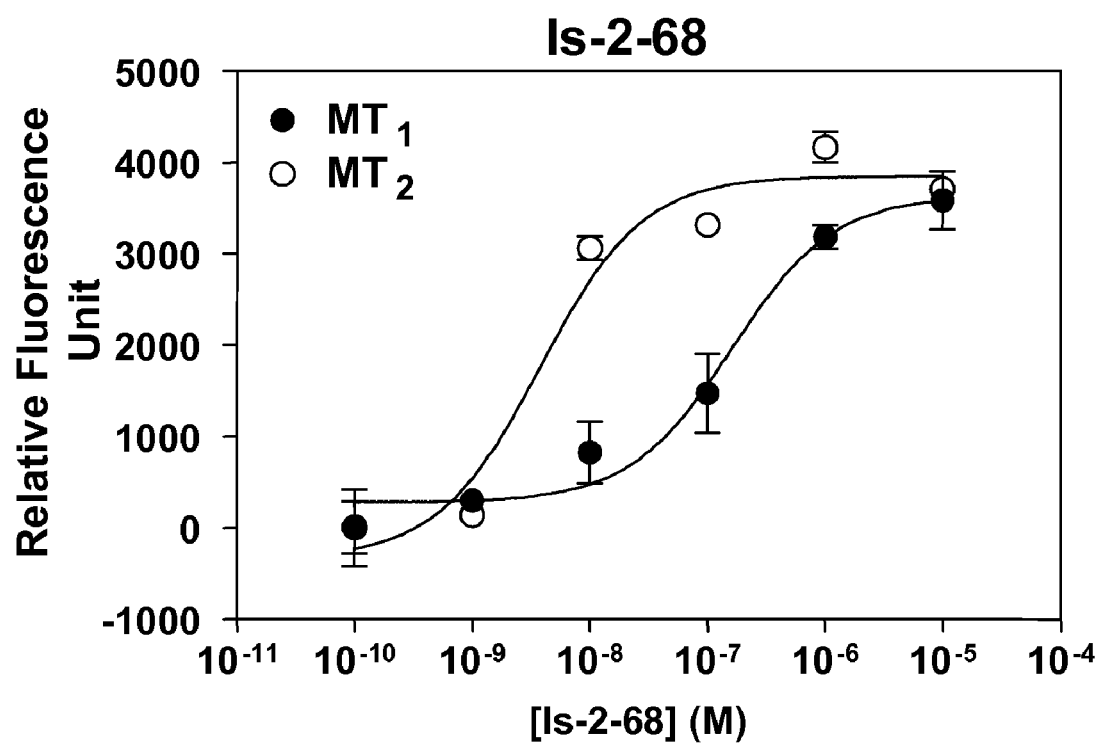
FIG. 5 shows a dose-response curve of Isoquinolone compound IS044.
Figure 6:
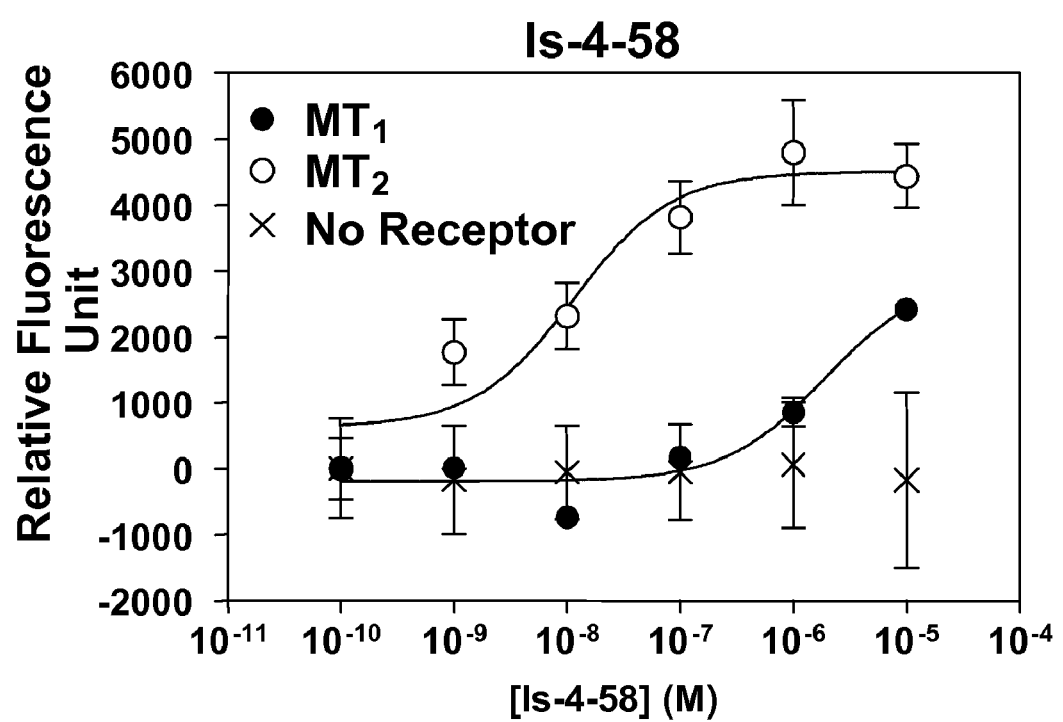
FIG. 6 shows a dose-response curve of Isoquinolone compound IS521.
Figure 7:
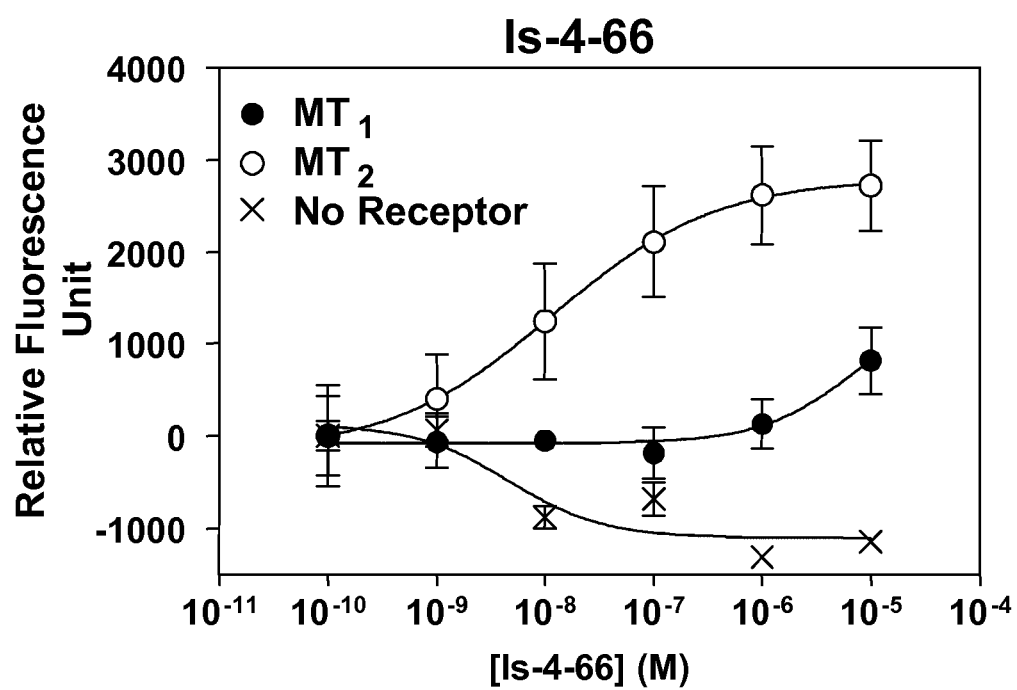
FIG. 7 shows a dose-response curve of Isoquinolone compound IS528.
Figure 8:
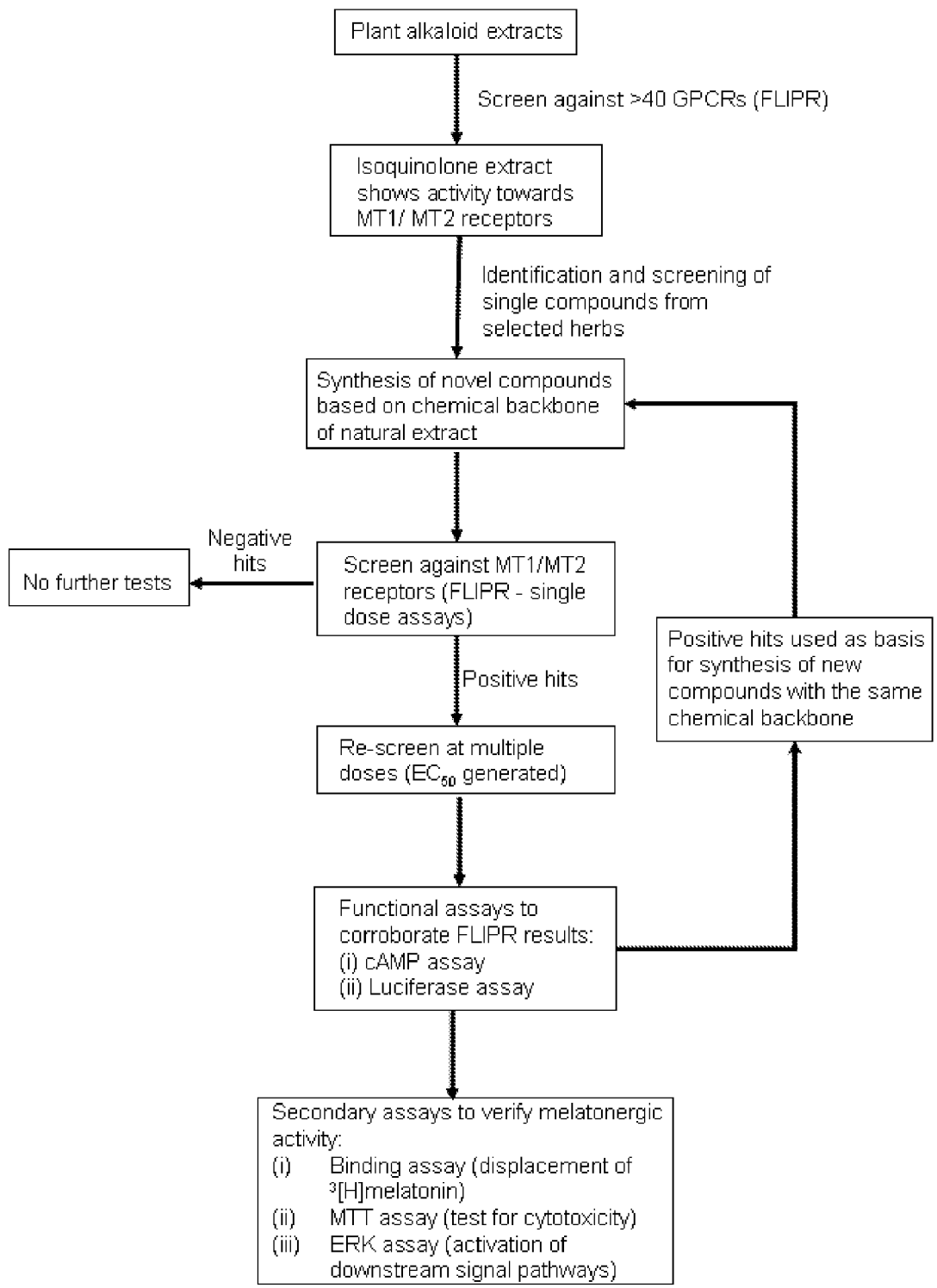
FIG. 8 presents the steps involved in developing novel melatonergic compounds of the present invention.

Referring to FIG. 8, alkaloids from natural products were first screened for specific activity towards G protein-coupled receptors (GPCR) via high-throughput screening ($Ca^{2+}$ mobilization assays) on a fluorometric imaging plate reader (FLIPR). A range of GPCR associated with key signaling pathways were used. Isoquinolone alkaloids, one of the most common types of alkaloids, exhibited activity towards the melatonin receptors, $MT_1$ and $MT_2$. A small library of compounds based on the isoquinolone alkaloids were then synthesized and screened against the $MT_1/MT_2$ receptors. Since these were preliminary screens, single dose assays (at 10 μM) were performed. Compounds that successfully activated the $MT_1/MT_2$ receptors were subjected to $Ca^{2+}$ mobilization assays again, this time through the use of parental cell lines. On this occasion, multiple doses of the novel compounds were used to generate complete dose-response curves and determine their corresponding $EC_{50}$s. A series of other functional assays were also performed on compounds exhibiting positive hits to obtain further proof of activity. These include the cAMP and luciferase assays.

All novel compounds that were successfully verified as melatonergic agonists were then subjected to secondary assays to confirm the mechanism of action. These include: (i) radioligand binding assay to examine the compounds ability to displace melatonin, the natural ligand of the $MT_1/MT_2$ receptors; and (ii) ERK assay to measure activation of downstream signal pathways. Furthermore, the novel compounds were also screened for cytotoxicity by means of an MTT assay, which measures cell viability after exposure to the novel isoquinolone compounds.

Synthetic schemes and specific examples of making compounds of the present invention are further provided in the following.

Scheme 1
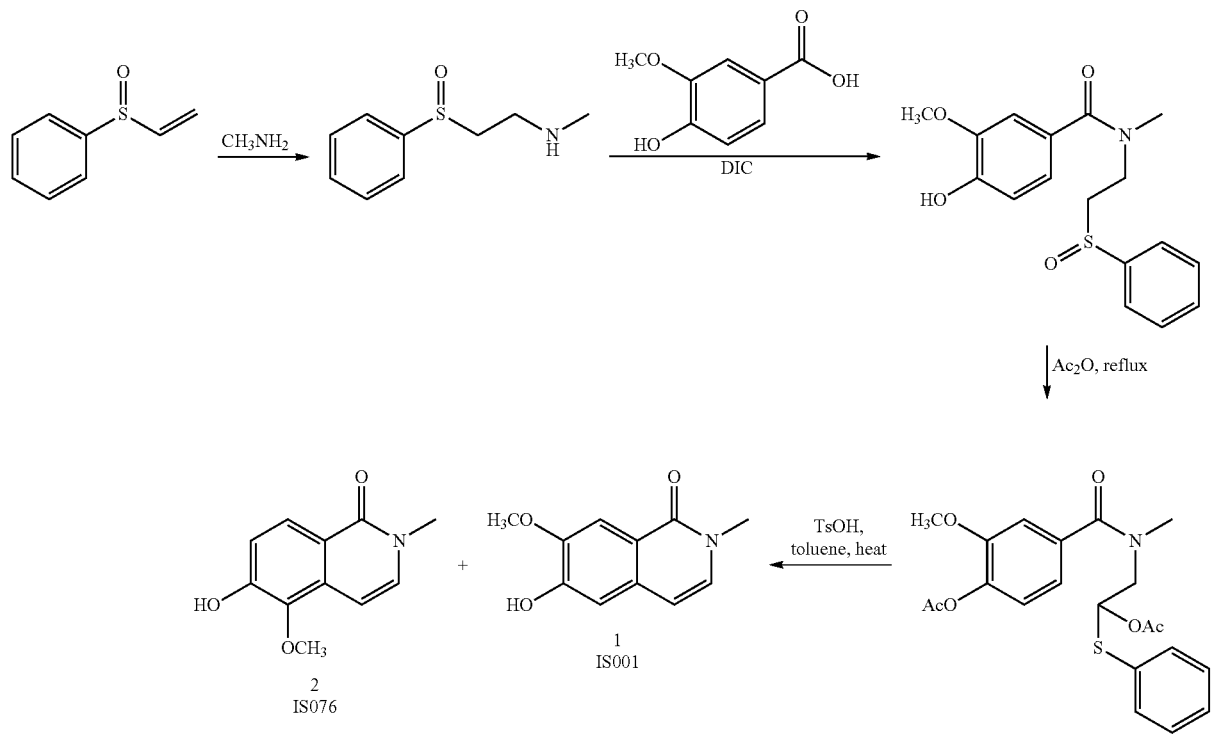
Scheme 1 is exemplified in Example 1 below.
Scheme 2
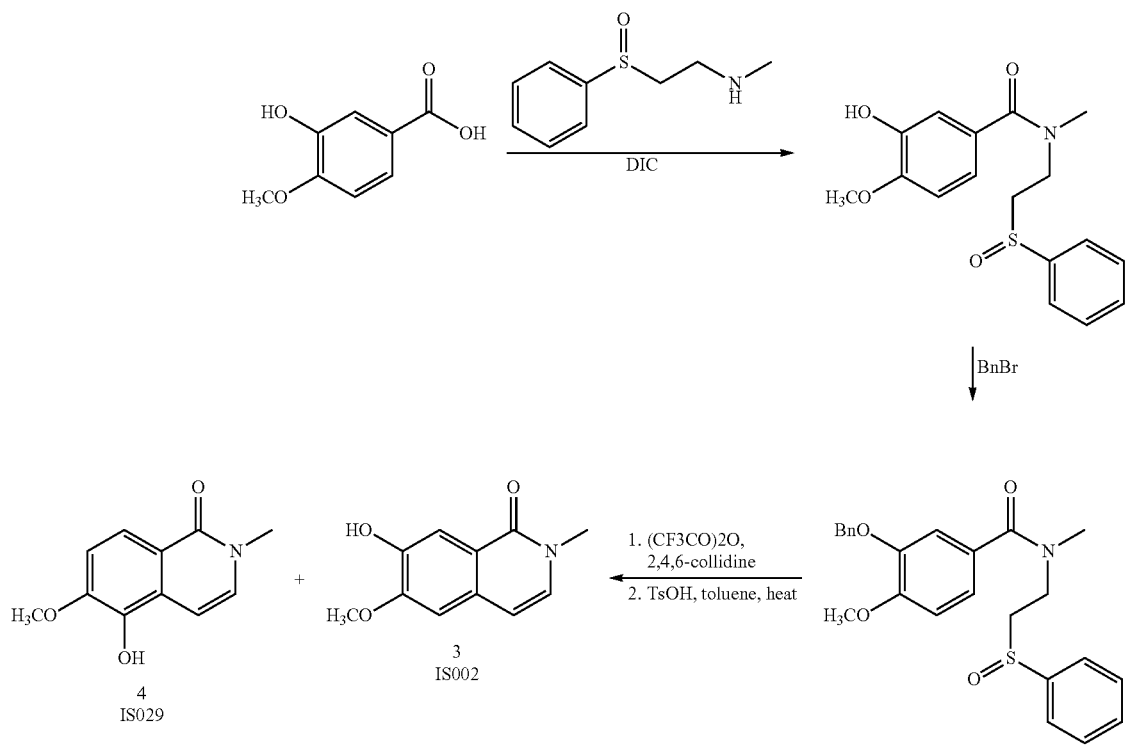

Scheme 2 is exemplified in Example 2 below.

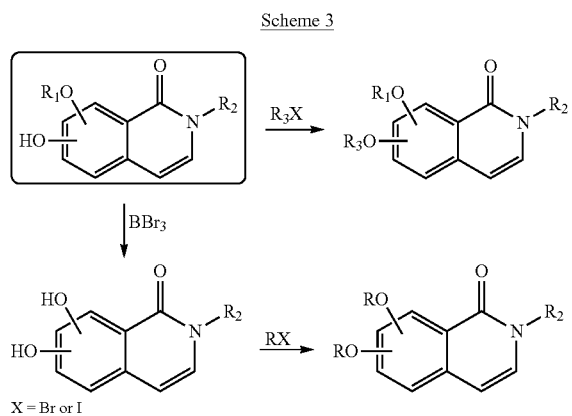

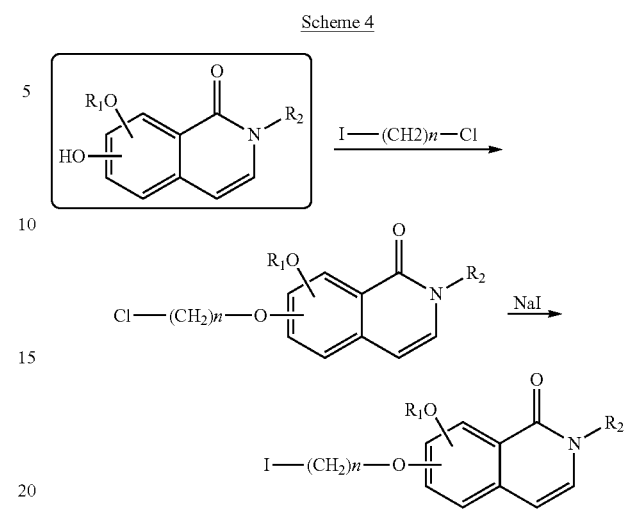

$R_1$, $R_2$ and $R_3$ are substituent groups that people of ordinary skill would deem suitable for the scheme. Preferably, $R_1$, $R_2$ are alkyl or substituted alkyl groups, and $R_3$, R are alkyl, substituted alkyl, acyl, sulphonyl groups. Scheme 3 is further exemplified in Examples 3 and 4 below.

R1 and R2 are substituent groups that people of ordinary skill would deem suitable for the scheme. n is 2-12. Scheme 4 is exemplified in Example 5 below.

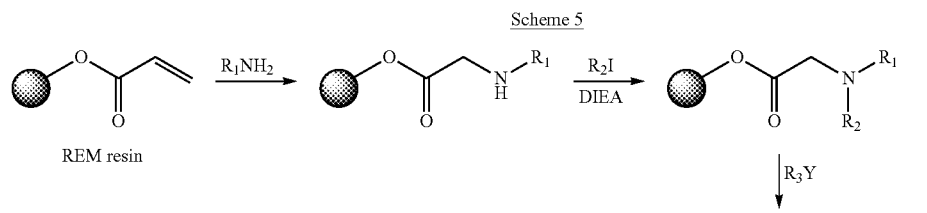

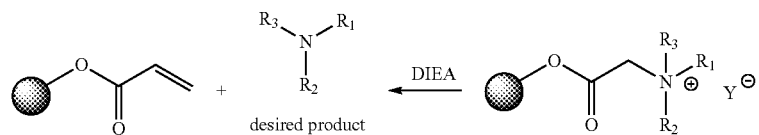

$R_1NH_2$: n-propylamine, n-butylamine, n-hexylamine, phenethylamine

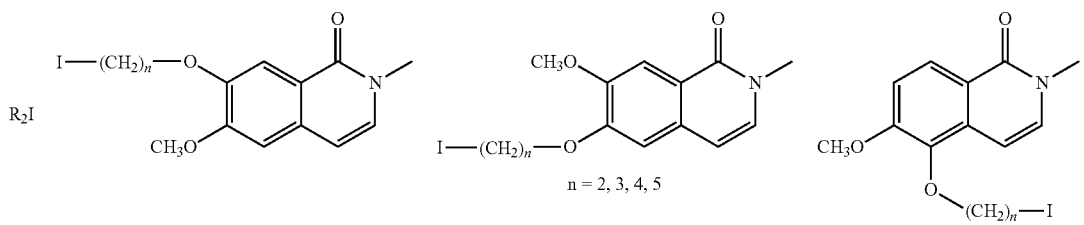

$R_3Y$: iodomethane, allyl bromide, benzylbromide, 4-bromobenzyl bromide, 3-methoxylbenzylbromide, 4-t-butylbenzyl bromide Scheme 5 is exemplified in Example 6 below.

SPECIFIC EXAMPLES

Example 1

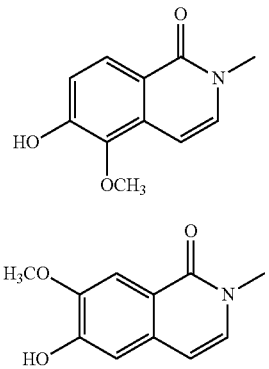

Step 1

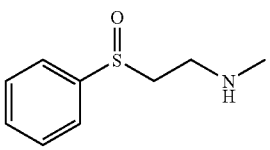

To a solution of methylamine in THF (2.0M, 16.8 mL, 33.7 mmol) was added phenyl vinyl sulfoxide (3 mL, 22.4 mmol). The reaction mixture was stirred at room temperature for 18 hours. The solvent was removed under vacuum. The resulting residue was purified by column chromatography to afford the product (2.9 g, 17.1 mmol, 76%).

Step 2

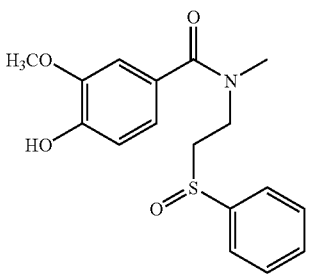 [SMILES: COc1cc(C(=O)N(C)CCS(=O)c2ccccc2)ccc1O]

To a solution of the product from step 1 (2.9 g), 4-hydroxy-3-methoxybenzoic acid (3.5 g, 20.6 mmol) and HOBt (2.8 g, 20.6 mmol) in 80 mL dichloromethane under nitrogen, was added diisopropylcarbodiimide (2.6 mL, 20.6 mmol) dropwise. The reaction was stirred at room temperature for 12 hours. The solvent was removed under vacuum. The resulting residue was purified by column chromatography to afford the product (4.8 g, 14.4 mmol, 84%). $^{1}$HNMR (400 MHz, CDCl$_3$) δ 7.64 (1H, dd, J=8.4, 1.2 Hz), 7.56 (1H, d, J=1.2 Hz), 7.30 (5H, m), 6.93 (1H, d, J=8.4 Hz), 4.49 (2H, t, J=5.6 Hz), 3.92 (3H, s), 3.31 (2H, t, J=5.6 Hz), 2.94 (3H, s).

Step 3

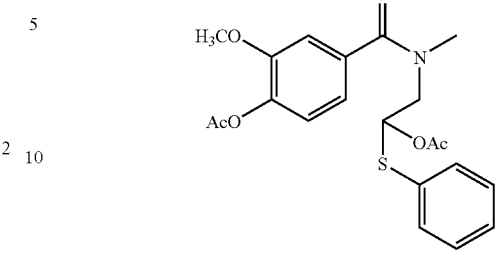

The product of step 2 (4.8 g, 14.4 mmol) was dissolved in 40 mL acetic anyhydride. The resulting mixture was heated at reflux for 6 hours. The excess acetic anhydride was removed under reduced pressure. The resulting residue was treated with saturated sodium bicarbonate, extracted with dichloromethane, dried and concentrated to afford the product (6.1 g, 100%), which was used in the next step without further purification. $^{1}$HNMR (400 MHz, CDCl$_3$) δ 7.53 (1H, m), 7.32 (4H, m), 7.01 (2H, m), 6.90 (1H, m), 6.50 (1H, s), 3.88 (2H, m), 3.81 (3H, s), 3.03 (3H, s), 2.32 (3H, s), 2.09 (3H, s).

Step 4

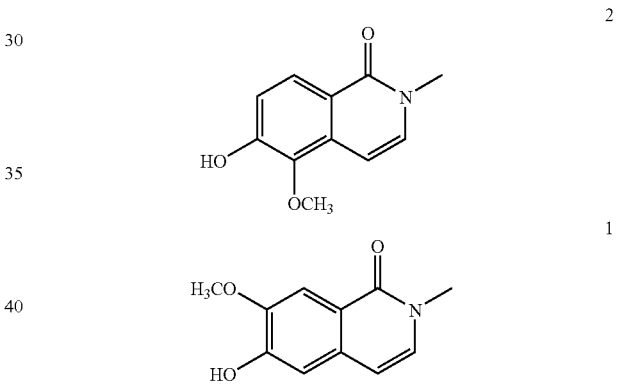

To a solution of the product of step 3 (crude 6.1 g) in 70 mL toluene, was added p-toluenesulfonic acid monohydrate (12.2 g, 64.1 mmol). The mixture was heated to reflux under nitrogen. After 40 minutes, the solvent was removed under reduced pressure. The resulting residue was neutralized with saturated sodium bicarbonate. The mixture was extracted with dichloromethane several times until TLC of the aqueous phase did not show the desired product. The combined dichloromethane was dried, concentrated and purified by column chromatography to afford two products as white solids.

Product 1: 6-Hydroxyl-7-methoxyl-2-methyl-1(2H)-isoquinolone (2.1 g, 10.2 mmol, 71%) $^{1}$HNMR (400 MHz, CDCl$_3$) δ 7.82 (1H, s), 6.99 (1H, s), 6.98 (1H, d, J=7.2 Hz), 6.38 (1H, d, J=7.2 Hz), 3.99 (3H, s), 3.60 (3H, s).

Product 2: 6-Hydroxyl-5-methoxyl-2-methyl-1(2H)-isoquinolone (80 mg, 0.39 mmol, 3%) $^{1}$HNMR (400 MHz, CDCl$_3$) δ 8.15 (1H, d, J=8.8 Hz), 7.15 (1H, d, J=8.8 Hz), 7.08 (1H, d, J=7.4 Hz), 6.66 (1H, d, J=7.4 Hz), 3.91 (3H, s), 3.59 (3H, s).

Starting with different substituted benzoic acids and primary amines, the following isoquinolone compounds with different substitution patterns were prepared according to the procedures outlined in Example 1.

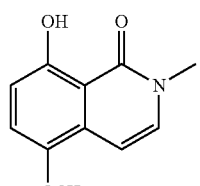

IS030

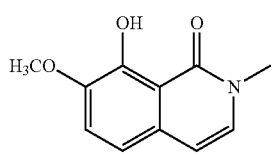

IS031

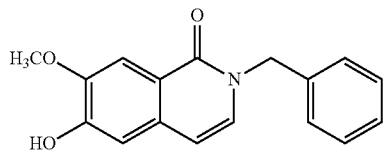

IS067

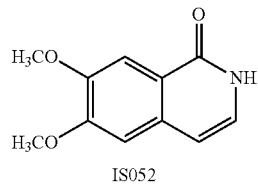

IS052

Example 2

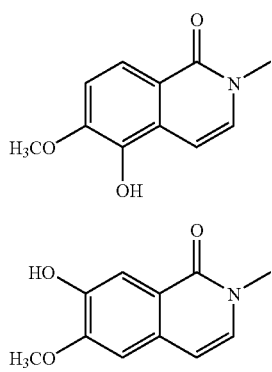

Step 1

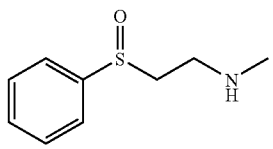

To a solution of methylamine in THF (2.0M, 49.3 mL, 98.5 mmol) was added phenyl vinyl sulphoxide (10 mL, 65.7 mmol). The reaction was stirred at room temperature for 48 hours. The mixture was concentrated under reduced pressure to give a crude product, which was purified by column chromatography to afford the product (8.38 g, 49.5 mmol, 75%).

Step 2

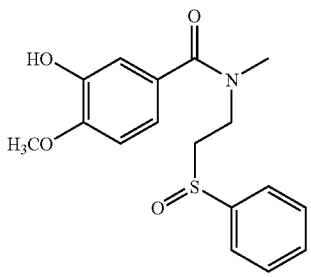 [SMILES: COc1ccc(C(=O)N(C)CCS(=O)c2ccccc2)cc1O]

To a solution of the product from step 1 (8.38 g, 45.7 mmol), 3-hydroxy-4-methoxyl-benzoic acid (8.46 g, 50.3 mmol) and HOBt (6.84 g, 50.3 mmol) in a mixture of 150 ml dichloromethane and 40 mL DMF, was added diisopropyl-carbodiimide (7.9 mL, 50.3 mmol) dropwise under nitrogen. After stirring at room temperature for 2 days, the reaction was stopped and concentrated under reduced pressure. The residue was treated with dichloromethane. The white urea salt was filtered off. The filtrate was treated with saturated ammonium chloride, extracted with dichloromethane, dried and concentrated to afford 18.83 g of crude product, which was used in the next step without further purification.

Step 3

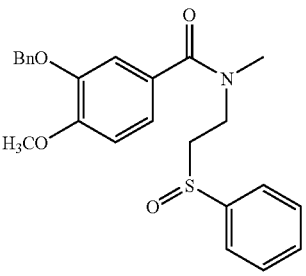 [SMILES: COc1ccc(C(=O)N(C)CCS(=O)c2ccccc2)cc1OCc1ccccc1]

To the product of step 2 (crude 18.83 g) in 100 mL DMF, was added benzyl bromide (8.1 mL, 68.6 mmol) and potassium carbonate (9.5 g, 68.6 mmol). The mixture was stirred at room temperature for 17 hours. The solvent was removed under reduced pressure and the resulting residue was treated with water, extracted with ethyl acetate (×3). The combined ethyl acetate extract was dried, filtered and concentrated. Purification by column chromatography afforded the product (17.7 g, 41.8 mmol, 91% for two steps).

Step 4

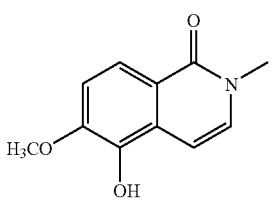

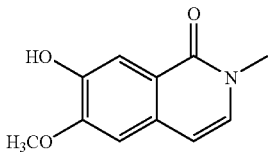

To a solution of the product of step 3 (17.7 g) in 210 mL dichloromethane under nitrogen at 0 degree Celsius, was added 2,4,6-collidine (16.6 mL, 125.4 mmol), followed by TFAA (29.5 mL, 208.95 mmol) dropwise. After stirring for 30 minutes, the reaction was quenched by slow addition of 180 mL 10% potassium carbonate. The mixture was then warmed to room temperature. The layers were separated. The aqueous layer was extracted with dichloromethane (×2). The combined dichloromethane was washed with 10% hydrochloride (×2), dried, filtered and concentrated.

The resulting residue was dissolved in 210 mL toluene. p-Toluenesulfonic acid monohydrate (39.75 g, 209.0 mmol) was added. The resulting mixture was heated at reflux for 40 minutes. The reaction was cooled to room temperature. Saturated sodium bicarbonate was added until pH=8. The layers were separated. The aqueous layer was extracted with dichloromethane several times until TLC of the aqueous layer did not show the desired products. The combined organic layers were dried, filtered and concentrated. Purification by column chromatography on silica gel afforded two major products.

Product 4: 5-hydroxyl-6-methoxyl-2-methyl-1(2H)-isoquinolone (2.5 g, 10 mmol, 24%). $^1$HNMR (400 MHz, CDCl$_3$) δ7.96 (1H, d, J=8.8 Hz), 7.03 (1H, d, J=8.8 Hz), 6.97 (1H, d, J=7.6 Hz), 6.83 (1H, d, J=7.6 Hz), 3.86 (3H, s), 3.55 (3H, s).

Product 3: 7-hydroxyl-6-methoxyl-2-methyl-1(2H)-isoquinolone (3.2 g, 15.6 mmol, 37%) $^1$HNMR (400 MHz, CDCl$_3$) δ7.78 (1H, s), 6.98 (1H, d, J=7.4 Hz), 6.87 (1H, s), 6.46 (1H, d, J=7.4 Hz), 3.98 (3H, s), 3.60 (3H, s).

Example 3

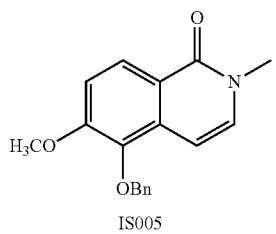

IS005

To a solution of 5-hydroxyl-6-methoxyl-2-methyl-1(2H)-isoquinolone (Product 4 from Example 2, step 4) (40 mg, 0.20 mmol) in 3 mL DMF, was added benzyl bromide (0.035 mL, 0.30 mmol) and potassium carbonate (55 mg, 0.40 mmol). The reaction was stirred at room temperature for 24 hours and quenched by addition of water. The mixture was extracted with ethyl acetate (×3), dried, filtered and concentrated. Purification of the resulting residue by column chromatography afforded the product (45 mg, 76%).

$^1$HNMR (400 MHz, CDCl$_3$) δ8.20 (1H, d, J=8.8 Hz), 7.35-7.47 (5H, m) 7.14 (1H, d, J=8.8 Hz), 6.94 (1H, d, J=7.0 Hz), 6.67 (1H, d, J=7.0 Hz), 5.07 (2H, s), 3.97 (3H, s), 3.53 (3H, s).

Using appropriate intermediate (Product 1, 2, 3, 4, 5, 6, 7 or 8) and different bromides (or iodides), the following compounds were prepared according to the procedure outlined in Example 3:

IS007, IS008, IS009, IS010, IS013, IS017, IS042, IS044, IS047, IS521, IS523, IS526, IS528, IS527, IS529, IS532, and IS098.

Example 4

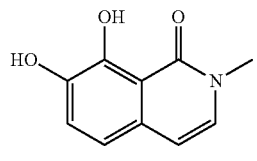

IS037

To a solution of 8-hydroxyl-7-methoxyl-2-methyl-1(2H)-isoquinolone (Product 6, 63 mg, 0.31 mmol) in 5 mL dichloromethane under nitrogen, was added boron tribromide (1.0M in dichloromethane, 3.1 mL). The reaction was stirred at room temperature for 4 hours and then quenched with methanol. The solvent was removed under reduced pressure and methanol was added. This procedure of addition of methanol followed by removal was repeated three times in order to remove boron residue. Purification by column chromatography on silica gel afforded the product (48.7 mg, 83%). $^1$HNMR (400 MHz, CD$_3$OD) δ 7.17 (1H, d, J=8.2 Hz), 7.01 (1H, d, J=7.4 Hz), 6.89 (1H, d, J=8.2 Hz), 6.51 (1H, d, J=7.4 Hz), 3.51 (3H, s).

Example 5

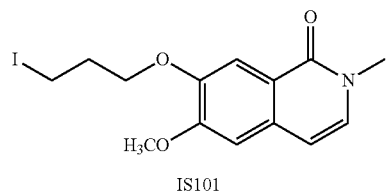 [SMILES: "IS101" ; COc1cc2ccn(C)c(=O)c2cc1OCCCI]

IS101

Step 1

Using product 3 (Example 2, step 4, 600 mg, 2.92 mmol) and 1-chloro-2-iodopropane (0.63 mL, 5.84 mmol) according to procedure outlined in Example 3, 7-(3-iodopropyloxyl)-6-methoxyl-2-methyl-1(2H)-isoquinolone (830 mg, 2.95 mmol, 100%) was prepared. ESI-MS 282.18 (M+1)

Step 2

To a solution of product from step 1 (830 mg, 2.95 mmol) in 29 mL methyl ethyl ketone, was added sodium iodide (4.41 g, 29.5 mmol). The reaction was heated at reflux for 30 hours. The solvent was removed under reduced pressure and water was added. The resulting mixture was extracted with dichloromethane (×3), dried, filtered and concentrated. Purification by column chromatography on silica gel afforded the product (1.01 g, 92%). ESI-MS 374.09 (M+1)

Example 6

Step 1

Stratosphere μL-REM resin, 50-100 mesh was evenly distributed into 96 IRORI microkan reactors. Each microkan reactor contained a radio refrequency tag and 28-35 mg resin. The 96 microkan reactors were sorted into four flasks. To each flask was added 40 mL dry DMF and one different amine (12.7 mmoL). The flasks were sealed and the microkan reactors were stirred at room temperature for 48 h. After DMF was removed, the microkan reactors were washed with DMF (×3), methylene chloride (×3) and methanol (×3) and dried under vacuum overnight.

Step 2

The 96 microkan reactors were sorted into four different flasks. To each flask was added 40 mL DMF, 1 mL diisopropylethylamine and one isoquinolone building block (prepared as shown in scheme 4). The flasks were sealed and stirred at 55 degree C. for 48 h. The reactions were stopped and the microkan reactors were washed with DMF (×3), methylene chloride (×3) and methanol (×3) and dried under vacuum overnight.

Step 3

The 96 microkan reactors were sorted into 6 different flasks. To each flask was added 20 mL DMF. Six different active halides were added to the six different flasks, respectively. After the flasks were shaked at room temperature for 24 h, the reactions were stopped. The microkan reactors were then washed with DMF (×3), methylene chloride (×3) and methanol (×3), methylene chloride (×3) and dried under vacuum overnight.

Step 4

Achived the 96 microkan reactors into 96 tube array. To each tube was added 2.1 mL of a mixture of 10 mL diisopropylethylamine in 200 mL methylene chloride. The 96 tube array was shaked at room temperature for 48 h, filtered into another 96 tube arrays. After the solvent was evaporated, the remaining residue was purified one by one through short silica gel column to obtain the final products. A library of 96 isoquinolone derivatives could be obtained through this 4-step reaction process from 4 amines, 4 isoquinolone building blocks and 6 halides.

Based on the above disclosed schemes and examples, isoquinolone derivatives with a variety of substituents attached to one or more positions of the isoquinolone backbone could be obtained. By varying the substitution of the starting benzoic acids, isoquinolone backbones with different substitution patterns could be prepared. Suitable libraries can also be built from isoquinolone building blocks, different amines and halides through solid phase combinatorial chemistry by using IRORI technology. These isoquinolone derivitives were then screened and compounds with greater specifity and efficacy than the patent compound were identified. Some screening assay methods are disclosed in the following.

II. Methods of Determining Melatonergic Agonist Activity

In general, two types of assays were performed in assessing the melatonergic activities of the compounds of the present invention:

Functional Assays:

1. FLIPR $Ca^{2+}$ Mobilization Assay

This assay indicates the ability of the novel compounds to activate $MT_1$ and $MT_2$ receptors by measuring downstream events of the activated receptor, in this case intracellular calcium mobilization. As indicated in Table 1, the $EC_{50}$ are in the μM-nM range. The response as a percentage of the 2-IMT response (a known melatonin agonist) is also included for the sake of comparison.

2. cAMP Assay

The cAMP assay indicates the ability of the novel compounds to activate melatonin receptors. When bound by an active agonist, melatonin receptors initiate a cascade of events which lead to an inhibition of cAMP production in cells. Cells expressing either the $MT_1$ or $MT_2$ receptor are treated with forskolin (a substance which stimulates cAMP production) alone or with a novel isoquinolone compound. The resulting percentage inhibition shown in Table 1 is a measure of melatonin receptor activation.

3. CRE-Luc Assay

The luciferase reporter gene assay offers another way to measure melatonin receptor activation. Cells expressing cAMP-responsive element-driven luciferase reporter gene (293-pCREluc) and either the $MT_1$ or $MT_2$ receptor are treated with forskolin (a substance which stimulates cAMP production as well as the subsequent luciferase gene expression) alone or with a novel isoquinolone compound. As melatonin receptor activation inhibits cAMP production, any suppression in the expression of luciferase leads to a decrease in enzymatic activities and a reduction in the amount of luminescence signal generated. The data in Table 1 indicates that inhibition is about 60-80% for majority of the novel isoquinolone compounds.

Secondary Assays:

1. Binding Assay

Competitive ligand binding assays were performed to examine the receptor binding characteristics of the novel isoquinolone compounds. The assay measures the ability of the novel isoquinolone compounds to bind and displace the radiolabelled endogenous ligand, [$^3$H]melatonin. Increasing concentrations of the novel compounds are added to displace the [$^3$H]melatonin-bound to $MT_1$ or $MT_2$ receptor-expressing cells. Provided that the novel compounds bind to the same region(s) of the receptor, the observed bound radioactivities will be diminished as the concentration of the novel compounds increase. As indicated in Table 2, 2-IMT (a known agonist with similar potencies towards both subtypes) displaces 85-95% of the bound [$^3$H]melatonin with an $IC_{50}$ of <1 nM. However, none of the isoquinolone compounds displace the bound melatonin indicating that receptor binding is at another site.

The binding assay results indicate that the novel compounds were not able, or only minimally able, to displace bound [$^3$H]melatonin, despite their high activity towards $MT_1$ or $MT_2$ receptors. Since isoquinolones are very different from the known melatoninergic ligand structures which are mainly are indole-based, the competitive binding assay results suggest that the binding characteristics of the isoquinolones are different from indoles. Therefore, rather than interacting with the $MT_1$ or $MT_2$ receptors at the same binding pocket on the receptor as the endogenous ligand melatonin (the orthosteric site), they may bind at a second allosteric site within the receptor that does not overlap with the melatonin binding site, leading to incomplete displacement of [$^3$H]melatonin. Allosteric sites are not uncommon in GPCR (they are found in some muscarinic subtypes, for example) but no previous report has indicated the existence of such sites in the melatonin receptors.

2. MTT Assay

This assay evaluates the cytotoxic effects of the novel isoquinolone compounds based on the cellular viability under chronic treatments. Viable cells but not dead cells can turn the substrate into a colored product, which yields higher absorbance. Data in Table 2 is expressed as the percentage of control cells (cells that have not been treated with the invention). A low percentage indicates low cytoviability (or high cytotoxicity).

3. ERK Phosphorylation Assay

This assay indicates the ability of the novel compounds to activate $MT_1$ or $MT_2$ receptors by measuring downstream events of the activated receptor, in this case ERK phosphorylation. The amount of phosphorylated ERK1/2 was detected and quantified in western blots. The data in Table 2 is expressed as the fold stimulation against the unstimulated control cells.

Some of the methods are described with greater details in the following:

1. Intracellular $Ca^{2+}$ Mobilization Assay Using Fluorometric Imaging Plate Reader (FLIPR®)

An intracellular calcium mobilization assay was performed to screen the isoquinolone compounds against the two melatonin receptor subtypes, $MT_1$ and $MT_2$ on the fluorometric imaging plate reader (FLIPR®). In order to facilitate the screening process in a high-throughput manner, chimeric G proteins with the ability to couple to a range of GPCR as well as activate intracellular $Ca^{2+}$ were employed. The melatonin receptor subtype (either $MT_1$ or $MT_2$) was co-expressed with the G-protein chimeras in COS-7 (monkey kidney fibroblast) cells. During the assay, cells were exposed to the novel isoquinolone compounds and the corresponding change in fluorescence was measured. Both single point and dose-dependant assays were performed for each isoquinolone compound and based on the latter a dose response curve was generated and the corresponding $EC_{50}$ for each receptor subtype determined.

Specifically, COS-7 cells were seeded at a density of 20,000 cells/well into 96-well plates designed for FLIPR assays, using Opti-MEM with 10% FCS at a volume of 100 μl/well. Transfection was carried out using Lipofectamine 2000® reagent. In each well, 0.2 μg of the GPCR and G protein cDNA were diluted with 25 μl of Opti-MEM and 0.2 μl of Lipofectamine 2000® was diluted with another 25 μl of Opti-MEM. They were added to appropriate wells after the two components were mixed for 20 min.

After 48 hours of incubation post-transfection, 50 μl of the transfection medium was removed from each well followed by the labelling of transfected cells with 100 μl of 2 μM Fluo-4 in calcium containing HBSS (Hank's balanced salt solution) with 20 mM HEPES (N-[2-hydroxyethyl]piperazine—N'-[2-ethanesulfonic acid]; pH 7.5) and 2.5 mM probenecid (anion exchanger inhibitor, freshly prepared) for 1 hour at 37° C. 70 μl of 3× drugs (isoquinolinone compounds encompassing the invention) were prepared and aliquoted into the corresponding wells in the V-well drug plate. Changes in fluorescence were detected in the FLIPR 96 with an excitation wavelength of 488 nm. The background fluorescence was adjusted to the range of 8,000 to 12,000 units by altering the laser power and exposure time (typically 0.4 W and 0.4 sec, respectively) for the FLIPR setup. 50 μl of each agonist solution was added to the corresponding wells and the fluorescent emission (between 510 and 560 nm) was monitored for 3 min. Results were expressed as change in fluorescent intensity units (FIU). Concentration-response curves were generated by determining the maximal change in FIU of each data set. Numerical analysis of the statistics and $EC_{50}$ (median effective concentration) values were performed on GraphPad Prism version 3.03.

2. CRE-Luciferase Assay

The luciferase assay, a reporter gene assay, was performed to confirm the ability of the invention to activate the melatonin receptors. Prior to the assay, HEK (human embryonic kidney) 293 cells are stably transfected with cAMP-responsive element-driven luciferase reporter gene (293-pCREluc) and cDNAs encoding $MT_1$ or $MT_2$ receptors. The cells are then exposed to the novel isoquinolone compounds, after which the substrate luciferin is added and the resulting luminescence measured.

Prior to the assay human embryonic kidney (HEK) 293 cells (CRL-1573, ATCC) is maintained at 37° C. in minimum essential medium (MEM) supplemented with 10% fetal bovine serum (FBS), 100 units/ml penicillin and 100 μg/ml streptomycin in a humidified atmosphere containing 5% $CO_2$. Human embryonic kidney 293 cells stably transfected with cAMP-responsive element-driven luciferase reporter gene (293-pCREluc) are established and maintained in growth medium supplemented with 300 μg/ml G418 sulphate.

For luciferase assays, HEK-293 cells stably expressing pCRE-luciferase are seeded at a density of 15,000 cells/well into 96 well plates. Transfection is carried out using Lipofectamine Plus® reagent at 0.2 μl of both Plus and lipofectamine reagents with 50 ng cDNAs encoding $MT_1$ or $MT_2$ receptors per well. After a 3 hour transfection period at 37° C., 50 μl of DMEM with 20% fetal calf serum (FCS) is added into the wells and the plate is incubated at 37° C. for 48 h prior to 24 hour serum starvation. Different novel isoquinolone compounds with 10 μM forskolin are added to the appropriate wells for 30 min followed by plain medium for another 6 hours.

Cells are harvested by replacing medium in the well by 50 μl luciferase lysis buffer. The Berthold microplate luminometer is maintained at 25° C. throughout the assay. Injector M connected to an empty tube and P connected to the drug tube are set to inject 25 μl of luciferin into appropriate wells. A 1.6 second delay time followed by a 1 second measuring time period is assigned to injector M, whereas injector P is measured for 10 seconds after luciferase substrate is introduced into the well. Results are expressed as relative luminescent units (RLU). Where indicated, agonist-induced activity is expressed as a percentage of the RLU obtained with forskolin.

3. [$^3$H]Cyclic AMP Assay

A cAMP assay is conducted to measure the level of the second messenger cAMP in cells expressing the melatonin receptor ($MT_1$ or $MT_2$) in the presence of the invention. When bound by an active agonist, melatonin receptors initiate a cascade of events which lead to an inhibition of cAMP in cells. Thus, a reduction in the level of cAMP in cells exposed to a compound of the invention compared to controls would indicate melatonin receptor activation. Stable CHO (Chinese hamster ovary) cell lines may be utilized.

The stable transfectant CHO-$MT_2$/16z25 expressing the melatonin $MT_2$ receptor and the G protein chimera 16z25 are maintained in growth medium supplemented with 300 μg/ml G418 sulphate and 200 μg/ml Zeocin®.

For the assay, CHO-$MT_2$/16z25 cells are seeded into 12-well cell culture plates at a cell density of $2 \times 10^5$/well and incubated overnight. Cells are labeled with [$^3$H]adenine (1 μCi/ml) in F12 medium with 1% FBS for another day. Labeled cells are washed with 1 ml of F12 medium with 20 mM HEPES, pH 7.5 and treated with 10 μM forskolin alone or with appropriate concentrations of tested compounds or 10 μM 2-IMT in the same medium with 1 mM 3-isobutyl-1-methylxanthine (phosphodiesterase inhibitor, freshly prepared) for 30 min. Reactions are stopped by aspiration and adding 1 ml chilled 5% trichloroacetic acid with 1 mM ATP to each well. Cells are lysed at 4° C. for at least 30 min and the [$^3$H]cAMP fraction is separated from other labeled adenosine nucleotides by sequential ion exchange chromatography. The cAMP levels are interpreted as the ratios of the counts per minute (cpm) of [$^3$H]cAMP fractions to those of the total labeled nucleotide fractions.

4. Competitive Binding Assay

The ability of compounds to bind to $MT_1$ and/or $MT_2$ receptors is determined using radioligand binding assays. HEK-293 cells are transfected with cDNAs encoding $G_{16z25}$ and either $MT_1$ or $MT_2$. 48 hours following transfection, cells are harvested in binding buffer (50 mM Tris-HCl, 2 mM MgCl2, 1 mM EDTA, pH 7.4). 100,000 cells are incubated with 1 nM [$^3$H] melatonin (specific activity: 83 Ci/mmol; GE Healthcare) and appropriate concentrations (0.1 nM to 1 µM) of unlabelled ligands in a total volume of 100 µl in 96-well plates (PerkinElmer Life And Analytical Sciences, Inc., Boston, Mass.) for 2 hours at room temperature. Reactions are terminated by rapid filtration through a 96-well cell harvester onto 96-well GF/C filter mats. Filters are washed with 500 µl of ice-cold binding buffer, dried and sealed in a polyethylene bag with 3.5 ml of scintillation fluid and counted for tritium in a Microbeta Jet scintillation counter. Each 96-well plate included a range of concentrations of the known melatonin receptor agonist 2-iodomelatonin as standards. Data are analyzed by nonlinear least-squares regression using GraphPad Prism 3.02.

5. Cytotoxicity Test Using MTT Assay

Cells were seeded into clear 96-well plate at an appropriate density in 100 µl growth medium and were allowed to grow overnight. The novel isoquinolone compounds were diluted to desired concentrations using fresh growth medium, and these dilutions were used to replace the growth media in each well. After incubating for 24-96 h, 10 µl of the MTT labeling reagent (Roche) was added to each well and the cells were incubated in a $CO_2$ incubator for 4 h. 100 µl solubilization buffer was then added into each well and incubated overnight for complete solubilization of the purple formazan crystals. Finally, the spectrophotometric absorbances of the samples at 570 nm were measured using an ELISA reader. Each condition was performed in triplicate in every experiment and the results were expressed as % of blank control±SD.

6. Detection of ERK phosphorylation

HEK293 cells expressing either melatonin receptor subtypes, seeded in confluence in 12-well plates a day before, were treated with 2-iodomelatonin (100 nM) or the selected novel isoquinolone derivative (1 µM) for 5 min. Stimulation was terminated by aspiration on ice and immediate lysis by 200 µl of 1× protein gel loading buffer. Lysates were denatured by boiling for 5 min and cooled at room temperature until loading. 30 µl of each lysate was separated on 12% SDS-PAGE and transferred to nitrocellulose membrane by electroblotting. Success of transfer was visualized by Ponceau S staining. All subsequent incubations were under gentle agitation (~100 strokes/min). Unused area of the membrane was blocked by "Blotto"—5% non-fat milk in 1× Tris-buffered saline (TBS). Primary antisera against phosphorylated- or total-ERK1/2 were incubated with the blocked membrane at an appropriate dilution (1:4000-1:2000) in Blotto for overnight at 4° C. The membrane was washed with fresh Blotto for 3 times of 15 min each, then incubated with secondary antiserum (horseradish peroxidase-conjugated anti-rabbit IgG) at the dilution of 1:1000 in 1×TBS for 1 h at room temperature. The membrane was quickly rinsed with excessive 1×TBS for 3 times, and followed by 4 washes of 1×TBS for 10 min. By the end, a premix of luminol-based chemiluminescence substrate solution was prepared (1 ml for every 8 $cm^2$ of membrane) and overlaid onto the washed membrane to incubate for 1 min. After removing excessive solution, the membrane was covered with saran wrap and an autograph with appropriate exposure was developed on X-ray film in dark room. The image was scanned and the band intensities quantified using ImageJ 1.34. Data was expressed as the percentage response of the vehicle-treated or untreated samples. Experiments were performed at least 3 times and the average responses±SEM were presented.

III Melatonergic Agonist Activity of Isoquinolone Derivatives of Present Invention In order to demonstrate the functional activity of the isoquinolone compounds in the library, the cDNAs of the $MT_1$ and $MT_2$ receptors were transfected into various cell lines. Then the intracellular $Ca^{2+}$ mobilization assays using the Fluorometric Imaging Plate Reader (FLIPR®) were performed as described above.

With reference to formula (III), the carbon atom position of the ring is counted clockwise with the carbon atom of the carbonyl group as C1 and thus R1, R2, R3, and R4 are attached to C5, C6, C7 and C8, respectively. Two major series of substituted isoquinolones, the 2,5,6- and the 2,6,7-substituted isoquinolones predominantly showed significant receptor-activating activity, while most of the derivatives appeared to be $MT_2$-specific. Variations of the substitutions on positions 5, 6 or 7 determined receptor subtype selectivity and receptor activation efficacy. The 2,5,6- and the 2,6,7-substituted isoquinolones mean an isoquinolone with substitutents at positions C2, C5 and C6 and isoquinolone with substitutents at positions C2, C6 and C7, respectively.

Referring to Table 1, the first series of compounds contained a methoxyl group at the C6 position with varying substitutions on the C5 position. A 5-benzyloxyl group substitution yielded a compound IS005 which bound to both melatonin receptors at nM affinity ($EC_{50}$: $MT_1$=5.81 nM; $MT_2$=48.5 nM), but with a slightly higher affinity to $MT_1$. However, IS005 seemed to be a partial agonist, as the activity was 31% and 63% for $MT_1$ and $MT_2$, respectively, compared to responses elicited by the known melatonin agonist, 2-iodomelatonin (2-IMT). A number of other substitutions, such as phenylpropyloxyl (IS008), p-bromobenzyloxyl (IS009), and p-methylbenzyloxyl (IS529), decreased the affinity and/or efficacy of receptor activation compared to a 5-benzyloxyl substitution, indicating that the extension of the alkyl chain was not tolerated well in the ligand binding pocket of the melatonin receptor. Importantly, these compounds activated $MT_2$ only, suggesting that the accommodation of the 5-substituted group is quite different in the two receptor subtypes.

At C5 position, mono- or di-meta substitutions to the benzene ring of the 5-benzyloxyl group with methoxyl group(s) significantly increased the affinity towards $MT_2$ (IS527: mono-meta, $EC_{50}$=5.78 nM; IS528: di-meta, $EC_{50}$=0.37 nM) without compromising their exclusive receptor subtype selectivity. IS528 and IS527 both partially activated $MT_2$, with ~65% efficacy compared to 2-IMT. Another highly $MT_2$-selective compound IS007 containing a 5-allyloxyl substitution, exhibited an $EC_{50}$ of 3.51 nM towards $MT_2$. Taken together with the findings for IS528 and IS527, this suggested that a diffused π-electron structure at the end of the 5-substitution facilitated the $MT_2$ selectivity of the isoquinolone compounds.

Similar substitutions were then made on C6 and C7, substituting either one with a methoxyl group. Benzyloxyl (C6: IS016 and C7: IS003) or phenylpropyloxyl (C6: IS017 and C7: IS013) substitutions on either position did not significantly increase the affinity compared with the compound: IS001 and IS002 (with hydroxyl groups at C6 and C7, respectively), and the $EC_{50}$'s ranged from 100 nM 1 µM. Whereas these substitutes resulted in full $MT_2$ agonists with similar maximal responses as that of 2-IMT, they showed weak or marginal activity to $MT_1$. Mono-(C6: IS044 and C7: IS521) and di-meta-methoxylbenzyloxyl (C6: IS042 and C7: IS523) substitutions on either position resulted in very potent full agonists with high $MT_2$ selectivity. Amongst these four derivatives, C6 substitutes showed a higher overall affinity to both receptor subtypes than C7 substitutes (1-2 orders lower $EC_{50}$). $MT_1$ had a better tolerance to C6 than C7 substitutes, but while C6 substitutes showed ~50% activation, C7 substitutes had very low efficacies (<30%). Di-meta-methoxylbenzyloxyl substitutes on either position appeared to have slightly higher maximal responses to $MT_2$, which were almost as good as 2-IMT. Conversely, mono-meta-methoxylbenzyloxyl substitutes elicited much higher responses than di-meta-methoxylbenzyloxyl substitutes in $MT_1$.

Further expansion on the variety of C5, C6 and C7 substitutions were conducted by combinatorial chemistry techniques. About 96 derivatives were produced for each position, which were then subjected to single-dose screening for melatonin receptor activation. However, only a few of them showed weak activation of both receptor subtypes. With the understanding of the ligand selectivity based on the finding mentioned above, this was not a surprising result as most of these derivatives were inactive due to the bulky substitutes at the 3 critical positions. Derivatives with substitutions on C4, C8 and N2 mostly demonstrated low affinity and/or efficacy to both receptor subtypes.

Overall, it was found that a 3-methoxylbenzyloxyl or 3,5-dimethoxylbenzyloxyl group at position C5, C6 or C7 of the isoquinolone scaffold was essential for an isoquinolone derivative to exhibit potent melatonin agonist activity. The compounds (IS527, IS528) with such a substituent attached at C5 position provided both high potency and $MT_2$ selectivity.

FIGS. 1-7 show dose-response curves for some representative isoquinolone compounds and their $EC_{50}$ for each receptor subtype: For isoquinolone compound IS005, the estimated $EC_{50}$ for $MT_1$ and $MT_2$ are $5.81 \times 10^{-9}$ nM and $4.85 \times 10^{-8}$ nM, respectively; for IS030, the estimated $EC_{50}$ for $MT_1$ and $MT_2$ are $1.04 \times 10^{-6}$ nM and $3.01 \times 10^{-6}$ nM, respectively; for IS007, the estimated $EC_{50}$ for $MT_2$ is $3.51 \times 10^{-9}$ nM ($MT_1$ undetermined); for IS017, the estimated $EC_{50}$ for $MT_2$ is $1.08 \times 10^{-7}$ nM ($MT_1$ undetermined); for IS044, the estimated $EC_{50}$ for $MT_1$ and $MT_2$ are $1.20 \times 10^{-8}$ nM and $3.79 \times 10^{-10}$ nM, respectively; for IS521, the estimated $EC_{50}$ for $MT_1$ and $MT_2$ are $1.86 \times 10^{-6}$ nM and $1.14 \times 10^{-8}$ nM, respectively; for IS528, the estimated $EC_{50}$ for $MT_1$ and $MT_2$ are $7.14 \times 10^{-6}$ nM and $3.69 \times 10^{-10}$ nM, respectively. Tables 1-3 present more testing data demonstrating melatonergic activities of the exemplary compounds of the present invention.

TABLE 1

Calcium mobilization via $MT_1/MT_2$ activation by some compounds of the present invention using the FLIPR $Ca^{2+}$ mobilization assay method described above

| | | | | | $MT_1$ | | |
| --- | --- | --- | --- | --- | --- | --- | --- |
| Name | R1 (C5) | R2 (C6) | R3 (C7) | R4 (C8) | Log($EC_{50}$) ± SEM | $EC_{50}$ (nM) | % Response of 2-IMT |
| IS005 | BnO | MeO | H | H | −8.24 ± 0.37 | $5.81 \times 10^{-9}$ | 30.5% |
| IS007 | $CH_2$=$CHCH_2$O | MeO | H | H | NSR | | |
| IS008 | PhPrO | MeO | H | H | NSR | | |
| IS009 | p-BrBnO | MeO | H | H | NSR | | |
| IS010 | p-MeO(Ph)$COCH_2$O | MeO | H | H | NSR | | |
| IS527 | m-MeOBnO | MeO | H | H | NSR | | |
| IS528 | m-$(MeO)_2$BnO | MeO | H | H | −5.15 ± 0.51 | $7.14 \times 10^{-6}$ | 42.1% |
| IS529 | p-MeBnO | MeO | H | H | NSR | | |
| IS532 | p-$(Me_3C)$BnO | MeO | H | H | NSR | | |
| IS002 | H | MeO | OH | H | −5.76 ± 2.56 | $1.74 \times 10^{-6}$ | 31.7% |
| IS003 | H | MeO | BnO | H | NSR | | |
| IS013 | H | MeO | Ph$(CH_2)_3$O | H | −5.22 ± 1.28 | $6.06 \times 10^{-6}$ | 75.0% |
| IS098 | H | MeO | Cl$(CH_2)_4$O | H | NSR | | |
| IS101 | H | MeO | I$(CH_2)_3$O | H | NSR | | |
| IS521 | H | MeO | m-MeOBnO | H | −5.73 ± 0.36 | $1.86 \times 10^{-6}$ | 31.8% |
| IS523 | H | MeO | m-$(MeO)_2$BnO | H | NSR | | |
| IS526 | H | MeO | p-$(Me_3C)$BnO | H | −5.35 ± 1.32 | $4.49 \times 10^{-6}$ | 46.2% |
| IS001 | H | OH | MeO | H | −5.80 ± 0.57 | $1.60 \times 10^{-6}$ | 71.9% |
| IS016 | H | BnO | MeO | H | −5.87 ± 0.40 | $1.34 \times 10^{-6}$ | 65.3% |
| IS017 | H | PhPrO | MeO | H | NSR | | |
| IS042 | H | m-$(MeO)_2$BnO | MeO | H | −7.92 ± 0.30 | $1.20 \times 10^{-8}$ | 49.4% |
| IS044 | H | m-MeOBnO | MeO | H | −6.79 ± 0.17 | $1.61 \times 10^{-7}$ | 54.5% |
| IS047 | H | m-$Me_2$BnO | MeO | H | −5.88 ± 2.61 | $1.33 \times 10^{-6}$ | 18.5% |
| IS030 | MeO | H | H | OH | −5.98 ± 0.04 | $1.04 \times 10^{-6}$ | 67.5% |
| IS037 | H | H | OH | OH | NSR | | |
| IS039 | H | PhCOO | PhCOO | H | NSR | | |

| | $MT_2$ | | | |
| --- | --- | --- | --- | --- |
| Name | Log($EC_{50}$) ± SEM | $EC_{50}$ (nM) | % Response of 2-IMT | $MT_2/MT_1$ $EC_{50}$ ratio |
| IS005 | −7.31 ± 0.17 | $4.85 \times 10^{-8}$ | 62.9% | 0.12 |
| IS007 | −8.46 ± 0.49 | $3.51 \times 10^{-9}$ | 49.1% | |
| IS008 | −6.25 ± 0.35 | $5.61 \times 10^{-7}$ | 57.6% | |
| IS009 | −6.91 ± 0.09 | $1.24 \times 10^{-7}$ | 37.4% | |
| IS010 | −6.35 ± 0.06 | $4.43 \times 10^{-7}$ | 53.0% | |
| IS527 | −8.24 ± 0.03 | $5.78 \times 10^{-9}$ | 65.9% | |
| IS528 | −9.43 ± 0.75 | $3.69 \times 10^{-10}$ | 64.8% | 19,300 |
| IS529 | −7.19 ± 0.10 | $6.52 \times 10^{-8}$ | 53.6% | |
| IS532 | −5.57 ± 0.75 | $2.70 \times 10^{-6}$ | 22.3% | |
| IS002 | −6.06 ± 0.27 | $8.67 \times 10^{-7}$ | 47.0% | 2.00 |

TABLE 1-continued

Calcium mobilization via $MT_1/MT_2$ activation by some compounds of the present invention using the FLIPR $Ca^{2+}$ mobilization assay method described above

| | | | | |
|---|---|---|---|---|
| IS003 | NSR | | | |
| IS013 | −6.00 ± 0.01 | $9.91 \times 10^{-7}$ | 101.9% | 6.11 |
| IS098 | −8.21 ± 0.57 | $6.14 \times 10^{-9}$ | 44.7% | |
| IS101 | −6.22 ± 0.48 | $5.99 \times 10^{-7}$ | 65.8% | |
| IS521 | −7.94 ± 0.36 | $1.14 \times 10^{-8}$ | 98.9% | 163 |
| IS523 | −7.34 ± 0.21 | $4.54 \times 10^{-8}$ | 61.0% | |
| IS526 | −5.42 ± 0.76 | $3.77 \times 10^{-6}$ | 88.6% | 1.19 |
| IS001 | NSR | | | |
| IS016 | −5.56 ± 0.14 | $2.73 \times 10^{-6}$ | 144.9% | 0.49 |
| IS017 | −6.97 ± 0.29 | $1.08 \times 10^{-7}$ | 106.6% | |
| IS042 | −9.42 ± 0.53 | $3.79 \times 10^{-10}$ | 84.5% | 31.7 |
| IS044 | −8.42 ± 0.25 | $3.80 \times 10^{-9}$ | 94.9% | 42.4 |
| IS047 | −5.98 ± 0.18 | $1.04 \times 10^{-6}$ | 94.1% | 1.28 |
| IS030 | −5.52 | $3.01 \times 10^{-6}$ | 39.4% | 0.35 |
| IS037 | −6.28 ± 0.36 | $5.27 \times 10^{-7}$ | 42.1% | |
| IS039 | −8.64 ± 0.20 | $2.31 \times 10^{-9}$ | 61.0% | |

NSR = no significant response

TABLE 2

Functional Assays Indicating Melatonergic Activity of Novel Isoquinolone Compounds

| | FLIPR $Ca^{2+}$ Mobilization Assay | | | | | |
|---|---|---|---|---|---|---|
| | MT1 | | | MT2 | | |
| Compound | logEC50 ± SEM | EC50 (M) | % Resp of 2-IMT | logEC50 ± SEM | EC50 (M) | % Resp of 2-IMT |
| IS039 | NSR | | | −8.64 ± 0.20 | 2.31E−09 | 61.0% |
| IS042 | −7.92 ± 0.30 | 1.20E−08 | 49.4% | −9.42 ± 0.53 | 3.79E−10 | 84.5% |
| IS044 | −6.79 ± 0.17 | 1.61E−07 | 54.5% | −8.42 ± 0.25 | 3.80E−09 | 94.9% |
| IS047 | −5.88 ± 2.61 | 1.33E−06 | 18.5% | −5.98 ± 0.18 | 1.04E−06 | 94.1% |
| IS521 | −5.73 ± 0.36 | 1.86E−06 | 31.8% | −7.94 ± 0.36 | 1.14E−08 | 98.9% |
| IS523 | NSR | | | −7.34 ± 0.21 | 4.543E−08 | 61.0% |
| IS526 | −5.35 ± 1.32 | 4.49E−06 | 46.2% | −5.42 ± 0.76 | 3.77E−06 | 88.6% |
| IS528 | −5.15 ± 0.51 | 7.14E−06 | 42.1% | −9.43 ± 0.75 | 3.69E−10 | 64.8% |
| IS527 | NSR | | | −8.24 ± 0.03 | 5.78E−09 | 65.9% |
| IS529 | NSR | | | −7.19 ± 0.10 | 6.52E−08 | 53.6% |
| 2-IMT | −9.78 ± 0.07 | 1.65E−10 | — | −9.23 ± 0.09 | 5.93E−10 | — |

| | cAMP Assay | | CRE-Luc Assay | |
|---|---|---|---|---|
| | | | MT1 | MT2 |
| Compound | MT1 % Inh | MT2 % Inh | % Inh ± SEM of 1 μM Fsk | % Inh ± SEM of 1 μM Fsk |
| IS039 | 8.8 ± 5.8 | 4.2 ± 6.8 | 73.0 ± 5.0 | 69.8 ± 7.2 |
| IS042 | 81.8 ± 6.2 | 58.7 ± 5.8 | 73.9 ± 7.8 | 71.3 ± 8.8 |
| IS044 | 72.9 ± 7.5 | 62.5 ± 4.0 | 82.3 ± 6.0 | 73.9 ± 12.4 |
| IS047 | 49.7 ± 18.6 | 60.7 ± 1.5 | 85.5 ± 5.5 | 80.2 ± 11.0 |
| IS521 | 19.4 ± 17.4 | 63.2 ± 4.9 | 84.2 ± 5.5 | 70.2 ± 9.2 |
| IS523 | 18.6 ± 14.7 | 50.8 ± 9.1 | 70.4 ± 5.6 | 71.6 ± 16.3 |
| IS526 | 26.9 ± 24.1 | −63.9 ± 59.2 | 36.2 ± 11.8 | 17.8 ± 4.7 |
| IS528 | 39.2 ± 12.0 | 49.4 ± 13.2 | 69.7 ± 10.1 | 60.8 ± 8.5 |
| IS527 | 28.3 ± 16.0 | 51.4 ± 12.1 | 82.4 ± 6.4 | 61.0 ± 9.3 |
| IS529 | 34.0 ± 17.4 | 37.7 ± 11.9 | 67.7 ± 5.4 | 61.3 ± 13.1 |
| 2-IMT | 48.5 ± 17.8 | 51.9 ± 5.6 | 73.0 ± 2.2 | 61.9 ± 5.0 |

NSR = No significant response

TABLE 3

Secondary Assays Verifying Melatonergic Activity of Novel Isoquinolone Compounds

| | Binding Assay | | | | | |
|---|---|---|---|---|---|---|
| | MT1 | | | MT2 | | |
| Compound | logIC50 ± SEM | IC50 | % Inh | logIC50 ± SEM | IC50 | % Inh |
| IS039 | NSB | | | NSB | | |
| IS042 | NSB | | | NSB | | |
| IS044 | NSB | | | −4.37 | 4.20E−05 | |
| IS047 | NSB | | | NSB | | |
| IS521 | NSB | | | −6.84 | 1.45E−07 | |
| IS523 | NSB | | | NSB | | |
| IS526 | NSB | | | NSB | | |
| IS528 | NSB | | | NSB | | |
| IS527 | NSB | | | −6.93 | 1.08E−07 | |
| IS529 | NSB | | | NSB | | |
| 2-IMT | −8.68 ± 0.23 | 2.11E−09 | 94.9% | −9.80 ± 0.13 | 1.58E−10 | 85.1% |

| | MTT Assay | | | ERK Phosphorylation | |
|---|---|---|---|---|---|
| | MT1/293 % Viability ± SEM | MT2/293 % Viability ± SEM | Parental 293 % Viability ± SEM | MT1 Fold Stim. | MT2 Fold Stim. |
| Compound | | | | | |
| IS039 | 108.5 ± 3.2 | 117.6 ± 9.0 | 104.9 ± 4.8 | 2.75 | 1.98 |
| IS042 | 71.6 ± 4.7 | 56.3 ± 1.5 | 60.7 ± 0.4 | 4.94 | 5.59 |
| IS044 | 112.6 ± 5.8 | 112.5 ± 3.8 | 78.6 ± 5.8 | 3.25 | 3.50 |
| IS047 | 40.2 ± 0.7 | 64.9 ± 31.9 | 69.1 ± 4.1 | 4.17 | 2.28 |
| IS521 | 89.8 ± 8.3 | 90.5 ± 11.7 | 66.1 ± 4.9 | 3.80 | 3.01 |
| IS523 | 51.6 ± 1.1 | 46.2 ± 3.7 | 37.5 ± 0.9 | 3.74 | 2.07 |
| IS526 | 25.0 ± 4.4 | 24.7 ± 1.6 | 27.5 ± 18.9 | | |
| IS528 | 50.2 ± 5.7 | 42.4 ± 1.3 | 32.2 ± 2.3 | 1.73 | 1.71 |
| IS527 | 57.1 ± 3.0 | 46.8 ± 0.2 | 36.8 ± 0.0 | 2.47 | 2.21 |
| IS529 | 54.9 ± 2.5 | 48.5 ± 1.6 | 35.9 ± 0.4 | 2.37 | 1.23 |
| 2-IMT | 113.3 ± 7.0 | 119.5 ± 8.3 | 105.9 ± 4.3 | 10.72 | 9.39 |

NSB = No significant binding

IV Manufacturing Pharmaceutical Compositions and their Uses in Treating Melatonin Receptor Related Disorders Once the effective chemical compound is identified and partially or substantially pure preparations of the compound are obtained, either by isolating the compound from natural resources such as plants or by chemical synthesis, various pharmaceutical compositions or formulations can be fabricated from partially or substantially pure compound using existing processes or future developed processes in the industry. Specific processes of making pharmaceutical formulations and dosage forms (including, but not limited to, tablet, capsule, injection, syrup) from chemical compounds are not part of the invention and people of ordinary skill in the art of the pharmaceutical industry are capable of applying one or more processes established in the industry to the practice of the present invention. Alternatively, people of ordinary skill in the art may modify the existing conventional processes to better suit the compounds of the present invention. For example, the patent or patent application databases provided on USPTO's official website contain rich resources concerning the manufacture of pharmaceutical formulations and products from effective chemical compounds.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of treating or ameliorating a pathological condition in a mammal, wherein said pathological condition is associated with a melatonin receptor, comprising a step of administering to said mammal a therapeutically effective amount of a compound of formula (I):

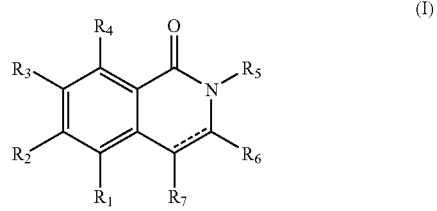

wherein $R_1$-$R_7$ are each independently hydrogen or a substituent.

2. The method according to claim 1, wherein
$R_1$, $R_2$, $R_3$, $R_4$ and $R_7$ are independently H, halo, alkoxy, alkyl or hydroxyl, provided that one of $R_1$, $R_2$, $R_3$ and $R_7$ is X—$(CH_2)_n$—$R_8$;
$R_5$ is alkyl or arylalkyl;
$R_6$ is H or alkyl;
X is a bond, O, S, SO, $SO_2$, CO or NH;
n=0-10;
$R_8$ is alkenyl, substituted or unsubstituted aryl, $NR_9R_{10}$, or $OR_9$;
$R_9$ is H, substituted or unsubstituted arylmethyl, or alkenyl; and
$R_{10}$ is H or alkyl.

3. A method of modulating an activity of a melatonin receptor, comprising a step of interacting with said receptor an effective amount of a compound of formula (I):

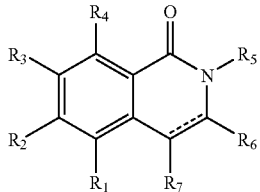

(I)

wherein $R_1$-$R_7$ are each independently hydrogen or a substituent.

4. The method according to claim 3, wherein $R_1$, $R_2$, $R_3$, $R_4$ and $R_7$ are independently H, halo, alkoxy, alkyl or hydroxyl, provided that one of $R_1$, $R_2$, $R_3$ and $R_7$ is X—$(CH_2)_n$—$R_8$;

$R_5$ is alkyl or arylalkyl;

$R_6$ is H or alkyl;

X is a bond, O, S, SO, $SO_2$, CO or NH;

n=0-10;

$R_8$ is alkenyl, substituted or unsubstituted aryl, $NR_9R_{10}$, or $OR_9$;

$R_9$ is H, substituted or unsubstituted arylmethyl, or alkenyl; and $R_{10}$ is H or alkyl.

5. A method of treating or ameliorating a pathological condition in a mammal, wherein said pathological condition is associated with a melatonin receptor, comprising a step of administering to said mammal a therapeutically effective amount of a compound of formula (II):

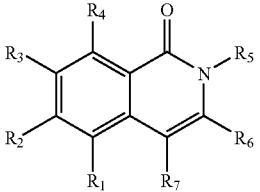

(II)

wherein $R_1$-$R_7$ are each independently hydrogen or a substituent.

6. A compound of formula (II):

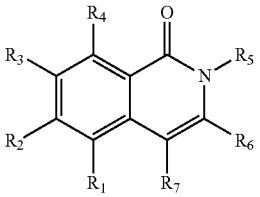

(II)

wherein $R_1$, $R_2$, $R_3$, $R_4$ and $R_7$ are independently H, halo, alkoxy, alkyl or hydroxyl, provided that one of $R_1$, $R_2$, $R_3$ and $R_7$ is X—$(CH_2)_n$—$R_8$;

$R_5$ is alkyl or arylalkyl;

$R_6$ is H or alkyl;

X is a bond, O, S, SO, $SO_2$, CO or NH;

n=1-10;

$R_8$ is alkenyl, substituted aryl, unsubstituted aryl, $NR_9R_{10}$, or $OR_9$;

$R_9$ is H, substituted arylmethyl, unsubstituted arylmethyl, or alkenyl; and $R_{10}$ is H or alkyl.

7. A compound according to claim 6, wherein $R_2$ is X—$(CH_2)_n$—$R_8$; and $R_1$, $R_3$, and $R_7$ are independently H, halo, alkyloxyl, alkyl or hydroxyl.

8. A compound according to claim 6, wherein $R_3$ is X—$(CH_2)_n$—$R_8$; and $R_1$, $R_2$, and $R_7$ are independently H, halo, alkyloxyl, alkyl or hydroxyl.

9. A compound according to claim 6, wherein $R_7$ is X—$(CH_2)_n$—$R_8$; and $R_1$, $R_2$, and $R_3$, are independently H, halo, alkyloxyl, alkyl or hydroxyl.

10. A compound according to claim 6, which is selected from the group consisting of:

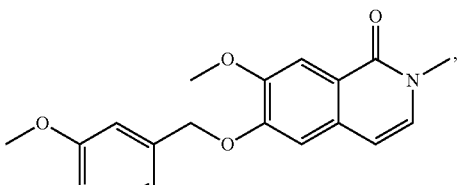

7-Methoxy-6-(3-methoxy-benzyloxy)-2-methyl-2H-isoquinolin-1-one

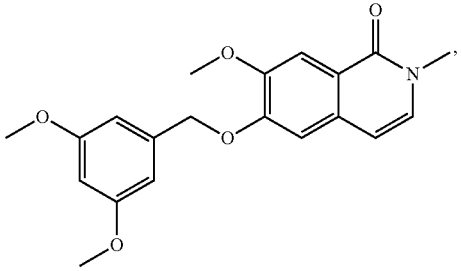

6-(3,5-Dimethoxy-benzyloxy)-7-methoxy-2-methyl-2H-isoquinolin-1-one

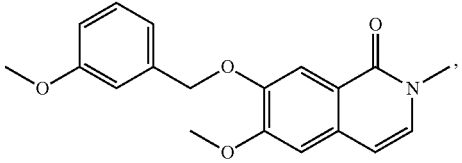

6-Methoxy-7-(3-methoxy-benzyloxy)-2-methyl-2H-isoquinolin-1-one

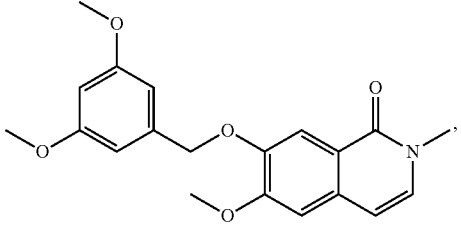

7-(3,5-Dimethoxy-benzyloxy)-6-methoxy-2-methyl-2H-isoquinolin-1-one

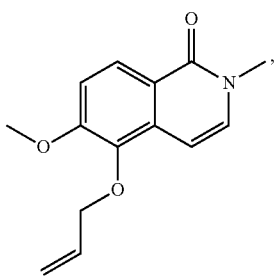

5-Allyloxy-6-methoxy-2-methyl-
2H-isoquinolin-1-one

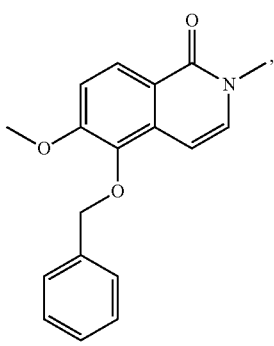

5-Benzyloxy-6-methoxy-2-methyl-
2H-isoquinolin-1-one

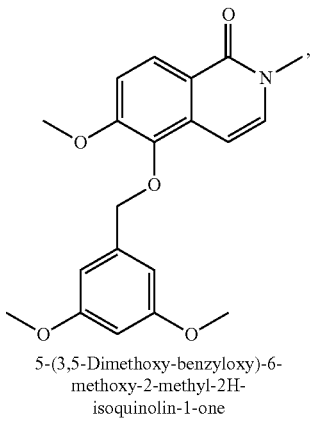

5-(3,5-Dimethoxy-benzyloxy)-6-
methoxy-2-methyl-2H-
isoquinolin-1-one

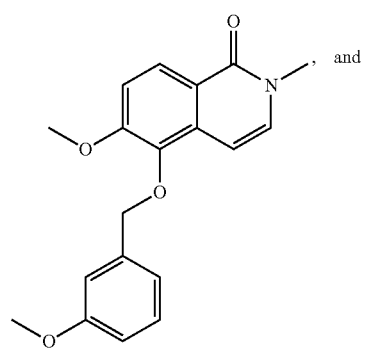

6-Methoxy-5-(3-methoxy-benzyloxy)-2-
methyl-2H-isoquinolin-1-one and

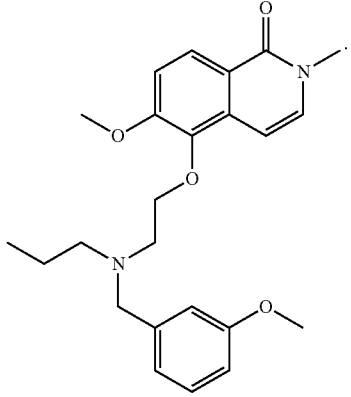

6-Methoxy-5-{2-[(3-methoxy-benzyl)-
propyl-amino]-ethoxy}-2-methyl-2H-
isoquinolin-1-one 11. A pharmaceutical composition, comprising a pharmaceutically acceptable carrier and a therapeutically effective amount of an active ingredient, wherein said active ingredient is a compound according to claim 6.

12. A pharmaceutical composition, comprising a pharmaceutically acceptable carrier and a therapeutically effective amount of an active ingredient, wherein said active ingredient is a compound of according to claim 7.

13. A pharmaceutical composition comprising a pharmaceutically acceptable carrier and a therapeutically effective amount of an active ingredient, wherein said active ingredient is a compound according to claim 8.

14. A pharmaceutical composition comprising a pharmaceutically acceptable carrier and a therapeutically effective amount of an active ingredient, wherein said active ingredient is a compound according to claim 9.

15. A pharmaceutical composition comprising a pharmaceutically acceptable carrier and a therapeutically effective amount of an active ingredient, wherein said active ingredient is a compound according to claim 10.

16. A method of modulating an activity of a melatonin receptor, comprising a step of interacting with said receptor an isoquinolone derivative, wherein said isoquinolone derivative is identified through a process comprising (a) making substitution at a position on an isoquinolone backbone that is a compound of formula (I) or formula (II) to obtain an isoquinolone derivative; and (b) performing an assay on said isoquinolone derivative to determine any effect related to a melatonin receptor or any melatonin agonist activity;

wherein the compound of formula (I) is:

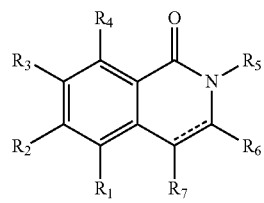

(I)

wherein $R_1$-$R_7$ of formula (I) are each independently hydrogen or a substituent; and wherein the compound of formula (II) is:

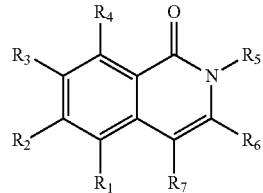

(II)

wherein $R_1$-$R_7$ of formula are each independently hydrogen or a substituent.

17. A compound according to claim 6, wherein
$R_1$ is X—$(CH_2)_n$—$R_8$; and
$R_2$, $R_3$, and $R_7$, are independently H, halo, alkyloxyl, alkyl or hydroxyl.

18. A pharmaceutical composition comprising a pharmaceutically acceptable carrier and a therapeutically effective amount of an active ingredient, wherein said active ingredient is a compound according to claim 17.

19. A method of modulating an activity of a melatonin receptor, comprising a step of interacting with said receptor an effective amount of a compound of formula (II):

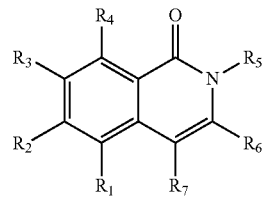

(II)

where $R_1$-$R_7$ are each independently hydrogen or a substituent.

20. The method according to claim 19, wherein
$R_1$, $R_2$, $R_3$, $R_4$ and $R_7$ are independently H, halo, alkoxy, alkyl or hydroxyl, provided that one of $R_1$, $R_2$, $R_3$ and $R_7$ is X—$(CH_2)_n$—$R_8$;
$R_5$ is alkyl or arylalkyl;
$R_6$ is H or alkyl;
X is a bond, O, S, SO, $SO_2$, CO or NH;
n=0-10;
$R_8$ is alkenyl, substituted or unsubstituted aryl, $NR_9R_{10}$, or $OR_9$;
$R_9$ is H, substituted or unsubstituted arylmethyl, or alkenyl; and
$R_{10}$ is H or alkyl.

* * * * *